United States Patent
Ito et al.

(10) Patent No.: US 7,803,534 B2
(45) Date of Patent: Sep. 28, 2010

(54) METHOD OF JUDGING BIOLOGICAL ACTIVITY IN BIOREMEDIATION SITE AND POLYNUCLEOTIDE FOR DETECTING MICROORGANISM TO BE USED THEREIN

(75) Inventors: Yoshitaka Ito, Aichi (JP); Kazuhiro Takamizawa, Gifu (JP); Hitoshi Iwahashi, Ibaraki (JP)

(73) Assignee: Panasonic Environmental Systems & Engineering Co., Ltd., Osaka (JP)

( * ) Notice: Subject to any disclaimer, the term of this patent is extended or adjusted under 35 U.S.C. 154(b) by 927 days.

(21) Appl. No.: 10/590,552

(22) PCT Filed: Feb. 25, 2005

(86) PCT No.: PCT/JP2005/003175

§ 371 (c)(1),
(2), (4) Date: Aug. 23, 2006

(87) PCT Pub. No.: WO2005/080600

PCT Pub. Date: Sep. 1, 2005

(65) Prior Publication Data

US 2007/0184448 A1    Aug. 9, 2007

(30) Foreign Application Priority Data

Feb. 25, 2004    (JP) .............................. 2004-050082
Feb. 25, 2004    (JP) .............................. 2004-050083

(51) Int. Cl.
*C12Q 1/68* (2006.01)
*C12P 19/34* (2006.01)

(52) U.S. Cl. ................. 435/6; 435/91.2; 435/252.3; 435/262.5; 435/287.2; 536/22.1; 536/23.5; 536/24.3; 588/300; 588/406

(58) Field of Classification Search ................. 435/6, 435/91.2, 252.3, 262.5, 287.2; 536/22.1, 536/24.3, 23.5; 588/300, 406
See application file for complete search history.

(56) References Cited

U.S. PATENT DOCUMENTS

2002/0150887 A1    10/2002    Maruyama et al.

(Continued)

FOREIGN PATENT DOCUMENTS

JP    2000-79000    3/2000

(Continued)

OTHER PUBLICATIONS

Denef et al, Validation of a more sensitive method for using spotted oligonucleotide DNA microarrays for functional genomic studies on bacterial communities, 2003, 5, 933-943.*

(Continued)

*Primary Examiner*—Stephen Kapushoc
*Assistant Examiner*—Narayan K Bhat
(74) *Attorney, Agent, or Firm*—Hamre, Schumann, Mueller & Larson, P.C.

(57) ABSTRACT

It is an object to provide a method whereby with respect to a microorganism present in an environment contaminated with tetrachloroethylene (PCE) and trichloroethylene (TCE), capability of the microorganism to degrade contaminants can be judged promptly.

In order to achieve the above-described object, a biological activity judging method according to the present invention is a method of judging capability of a contaminated environment to eliminate an organochlorine compound, in which using a DNA probe that allows a bacterium to be detected specifically, which has a degradation activity with respect to the organochlorine compound and/or a dechlorinated product thereof, the bacterium in the environment is detected.

The present invention also provides a new type of polynucleotide that can be used as a DNA probe in the biological activity judging method according to the present invention.

3 Claims, 5 Drawing Sheets

U.S. PATENT DOCUMENTS

2003/0077601 A1* 4/2003 Ebersole et al. ............ 435/6
2005/0048524 A1 3/2005 Hiraishi

FOREIGN PATENT DOCUMENTS

JP 2000-253886 9/2000
JP 2003-154332 5/2003
JP 2004-290171 10/2004

OTHER PUBLICATIONS

Buck et al, Design strategies and performance of custom DNA sequencing primers, 1999, BioTechniques, 27, 528-536.*

Scott et al, Construction of ITS sequence based oligonucleotide microarray for the detection of bacteria associated with PCE bioremediation., 2004, Nippon Mizu Kankyo Gokka Nenkai Koenshu, 38, p. 75.*

Scott et al, poster materials presented at the Society for Biotechnology, Japan, 2003, pp. 11-33.*

Chang et al., "Recent Developments in Studies on PCE-Degrading Microorganisms (1)" Environmental Conservation Engineering, 2000, vol. 29, No. 8, pp. 642-649 (with partial translation).

Chang, et al., "Recent Developments in Studies on PCE-Degrading Microorganisms(2)" Environmental Conservation Engineering, 2000, vol. 29, No. 9, pp. 725-732 (with partial translation).

Kuwahara, et al., "*Genetic Variation in 16S-23S rDNA Internal Transcribed SpacerRegions and the Possible Use of This Genetic Veriation for Molecular Diagnosis of Bacteroides Species*", Microbiol. Immunol. vol. 45, No. 3, p. 191-199, 2001.

Selvarangan, et al., "*Rapid Identification of Commonly Encountered Candida Species Directly from Blood Culture Bottles*", J. Clin. Microbiol., 2003, vol. 41 No. 12, p. 5660-5664.

Frothingham, et al., "*Sequence-Based Differentiation of Strains in the Mycobacterium avium Complex*", J. Bacteriol., 1993, vol. 175, No. 10, p. 2818-2825.

Randolph Scott, et al., "*Construction of a 16S-23S ribosomal DNA internal transcribed spacer sequence (16S-23S rDNA-ITS)-based microarray for the detection of percholoroethylene (PCE)-degrading microorganisms*", The Society for Biotechnology, Japan, Extended Abstracts (The 55$^{th}$ Meeting, 2003), 2J09-3.

Trust, et al., "Phylogenetic and Molecular Characterization of a 23 S rRNA Gene Positions the Genus *Campylobacter* in the Epsilon Subdivision of the *Proteobacteria* and Shows that the Presence of Transcribed spacers is Common in *Campylobacter* spp.", Journal of Bacteriolgy, vol. 176, No. 15, Aug. 1994, pp. 4597-4609.

* cited by examiner

A probes (for *Dehalospirillum multivorans*)

M probes (for *Dehalobacter restrictus*)

B probes (for *Desulfitobacterium frappieri*)

N probes (for *Desulfitobacterium* PCE1)

I probes (for *Desulfitobacterium hafniense*)

O probes (for *Desulfitobacterium frappieri* TCE1)

J probes (for *Clostridium formicoaceticum*)

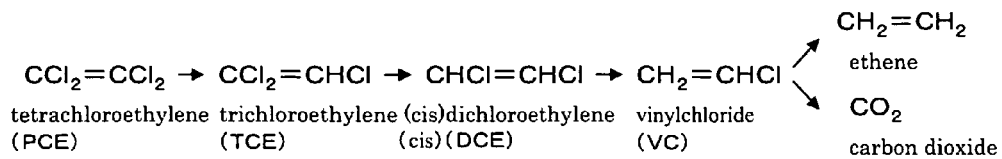

tetrachloroethylene $CCl_2=CCl_2 \rightarrow$ trichloroethylene $CCl_2=CHCl \rightarrow$ (cis)dichloroethylene $CHCl=CHCl \rightarrow$ vinylchloride $CH_2=CHCl$ $\nearrow CH_2=CH_2$ ethene $\searrow CO_2$ carbon dioxide
(PCE) (TCE) (cis)(DCE) (VC)

FIG. 5A

| Dehalococcoides ethenogenes 195 R | PCE → TCE → DCE → VC → ethene |
|---|---|
| Desulfitobacterium frappieri B | PCE → TCE → cisDCE |
| Desulfitobacterium hafniense I | |
| Desulfitobacterium dehalogenans H | |
| Desulfitobacterium sp. strain PCE1 N | |
| Desulfitobacterium frappieri TCE1 O | |
| Desulfomonile tiedjei DCB-1 Q | |
| Desulfuromonas chloroethenica K | PCE → TCE→ DCE |
| Acetobacterium woodii L | PCE → TCE |
| Acetobacterium woodii P | |
| Clostridium formicoaceticum J | PCE → TCE |
| Dehalobacter restrictus M | PCE → cisDCE |
| Dehalospirillum multivorans A | PCE → cisDCE |
| Desulfomicrobium norvegicum G | PCE → cisDCE |
| Rhodococcus sp. Sm-1 C | DEC, VC → CO2 |
| Rhodococcus rhodococcus D | |
| Xanthobacter flavus E | DCE, VC → CO2 |
| Mycobacterium L1 F | VC → CO2 |

FIG. 5B

METHOD OF JUDGING BIOLOGICAL ACTIVITY IN BIOREMEDIATION SITE AND POLYNUCLEOTIDE FOR DETECTING MICROORGANISM TO BE USED THEREIN

The patent or application file contains at least one drawing executed in color. Copies of this patent or patent application publication with color drawing(s) will be provided by the Office upon request and payment of the necessary fee.

TECHNICAL FIELD

The present invention relates to a method of judging a biological activity at a bioremediation site and a polynucleotide for detecting a microorganism used therein.

BACKGROUND ART

Contamination of groundwater and soil with various types of organochlorine compounds including tetrachloroethylene (PCE) and trichloroethylene (TCE) has been a serious issue around the globe. This issue often has been covered thoroughly by mass media such as newspapers and the like, leading to a strong social demand for development of technologies for remedying environments contaminated with these substances.

Such technologies for remedying a contaminated environment include a physicochemical method and a biological method. Among these methods, particularly suited for remediation with respect to low-level contamination is the biological method of remedying an environment using a microorganism (bioremediation). Bioremediation is widely expected to be put to practical use since it can be performed at low cost without requiring soil excavation, allows even an environment under a building to be remedied easily, and achieves a reduction in environmental burdens.

Bioremediation is performed in the following manners. That is, for example, various nutritive substances or the like are supplied to microorganisms originally inhabiting contaminated soil or groundwater so that the capability of the microorganisms to degrade and eliminate environmental contaminants is enhanced (biostimulation). Alternatively, microorganisms having the capability to degrade and eliminate environmental contaminants are introduced directly into a contaminated environment (bioaugmentation: JP 2003-154332 A, for example). An example also is known in which biostimulation and bioaugmentation were used to remedy an environment that was groundwater contaminated with TCE, yielding excellent results.

In implementing bioremediation, it is judged whether a contaminated site can be treated with biostimulation or should be treated with bioaugmentation in which microorganisms having the capability to degrade contaminants are introduced from outside of a system, and it has been desired that such judgment be performed promptly (JP 2000-079000 A, for example).

DISCLOSURE OF INVENTION

Problem to be Solved by the Invention

With the foregoing in mind, it is an object of the present invention to provide a method whereby a microorganism in an environment contaminated with tetrachloroethylene (PCE) and trichloroethylene (TCE) is detected and the capability of the environment to degrade contaminants (a biological activity) can be judged promptly, and a polynucleotide for detecting a microorganism used in the judging method.

Means for Solving Problem

In order to achieve the above-described object, a method of judging a biological activity in an environment according to the present invention is a method of judging a biological activity in an environment contaminated with an organochlorine compound that is at least one of PCE and TCE. The method includes: amplifying a nucleic acid extracted from an environmental sample by a gene amplification method so as to use the nucleic acid as a target; hybridizing the target to at least one DNA probe including a base sequence unique to each of at least one type of bacterium related to degradation of the organochlorine compound so that the at least one type of bacterium in the environment is detected; and judging the capability of the environment to eliminate the organochlorine compound based on the degrading capability of the at least one type of bacterium that is detected with respect to the organochlorine compound and a dechlorinated product of the organochlorine compound.

The at least one DNA probe includes one or more DNA probes containing a polynucleotide according to the present invention, i.e. any one of the types of polynucleotides described below in (1) to (4).

(1) A polynucleotide comprising any one of base sequences represented by SEQ ID NOS: 1 to 17 and SEQ ID NOS: 19 to 105 of the Sequence Listing, respectively.

(2) A polynucleotide comprising a base sequence obtained by deletion, substitution or insertion of one to several bases in the base sequence of the polynucleotide described in (1), which is hybridizable to a polynucleotide comprising a base sequence complementary to the polynucleotide described in (1) under a stringent condition.

(3) A polynucleotide comprising a base sequence obtained by deletion, substitution or insertion of one to several bases in the base sequence of the polynucleotide described in (1), which has a homology of 90% or higher with the polynucleotide described in (1).

(4) A polynucleotide comprising a base sequence complementary to any one of the polynucleotides described in (1) to (3).

Furthermore, the at least one type of bacterium related to degradation of the organochlorine compound that is to be detected in the present invention includes one or more types of anaerobic bacteria selected from a group consisting of types of bacteria denoted below as A to R.

A: *Dehalospirillum multivorans*

B: *Desulfitobacterium frappieri*

C: Actinomycetales Sm-1 (*Rhodococcus* sp. Sm-1)

D: *Rhodococcus rhodococcus*

E: *Xanthobacter flavus*

F: *Mycobacterium* L1

G: *Desulfomicrobium norvegicum* (*Desulfovibrio baculatus*)

H: *Desulfitobacterium dehalogenans*

I: *Desulfitobacterium hafniense*

J: *Clostridium formicoaceticum*

K: *Desulfuromonas chloroethenica*

L: *Acetobacterium woodii* DSM 1030

M: *Dehalobacter restrictus*

N: *Desulfitobacterium* sp. strain PCE1

O: *Desulfitobacterium frappieri* TCE1

P: *Acetobacterium woodii* DSM 2396

Q: *Desulfomonile tiedjei* DCB-1

R: *Dehalococcoides ethenogenes* 195

Effects of the Invention

In relation to bioremediation with respect to an environment contaminated with an organochlorine compound such as PCE, TCE or the like, if an anaerobic bacterium capable of degrading the organochlorine compound and a dechlorinated product thereof can be detected promptly from the contaminated environment, an assessment of whether biostimulation can be performed or bioaugmentation should be performed is facilitated. The inventors of the present invention took note of this fact and conducted vigorous studies on a method of detecting the currently known 18 types of anaerobic bacteria capable of degrading organochlorine compounds and dechlorinated products thereof (the types of bacteria denoted as A to R; hereinafter, referred to also as anaerobic bacteria related to degradation of organochlorine compounds).

As a result of the studies, the inventors found that each of the types of bacteria denoted as A to R has specificity in terms of base sequences in an ITS region (SEQ ID NOS: 1 to 18 of the Sequence Listing) that is a genome region common to the types of bacteria denoted as A to R, and the use of a DNA probe containing a polynucleotide based on the base sequences allows each of the types of bacteria denoted as A to R to be detected using a genetic detection technique such as, for example, a DNA microarray.

The inventors of the present invention conducted further studies to determine, based on the base sequences in the respective ITS regions of the 18 types of bacteria denoted as A to R (SEQ ID NOS: 1 to 18 of the Sequence Listing), specific base sequences of a length that can be used suitably for, for example, a DNA microarray, with which the types of bacteria denoted as A to R can be detected at the same time without cross-reacting with one another (SEQ ID NOS: 19 to 115 of the Sequence Listing), thus arriving at the present invention.

The ITS region refers to a transcribed region between a 16S ribosomal DNA and a 23S ribosomal DNA of a bacteria genome occurs (Internal Transcribed Spacer). The base sequences in the respective ITS regions of the types of bacteria denoted as A to Q (assigned SEQ ID NOS: 1 to 17, respectively) were determined for the first time by the inventors of the present invention.

According to the present invention, a bacterium related to degradation of an organochlorine compound in a contaminated environment is detected promptly using a DNA probe, and based on the degrading capability of the bacterium (see, for example, FIG. 5B), the capability of the environment to eliminate PCE and a dechlorinated product thereof can be judged. Therefore, according to the present invention, in implementing bioremediation, an assessment of whether biostimulation can be performed or bioaugmentation should be performed is facilitated, thereby allowing the selection of a proper method of remedying an environment. Moreover, since a method of remedying an environment is selected promptly and properly, remediation of the environment can be performed at low cost.

It is thought that PCE hardly is degraded under an aerobic condition. Further, generally, an environment 50 cm or more below the surface of the Earth is believed to be anaerobic. Therefore, in remedying an environment contaminated with PCE or a contaminated environment 50 cm or more below the surface of the Earth, the use of an aerobic microorganism instead of an anaerobic microorganism that essentially is applicable may incur extra cost and energy consumption. The present invention can avoid incurring such extra cost and energy use.

BRIEF DESCRIPTION OF DRAWINGS

FIG. 5A is a diagram illustrating a degradation route of PCE.

FIG. 5B is a diagram explaining degradation activities of bacteria A to R with respect to organochlorine compounds.

DESCRIPTION OF THE INVENTION

Figure 1:
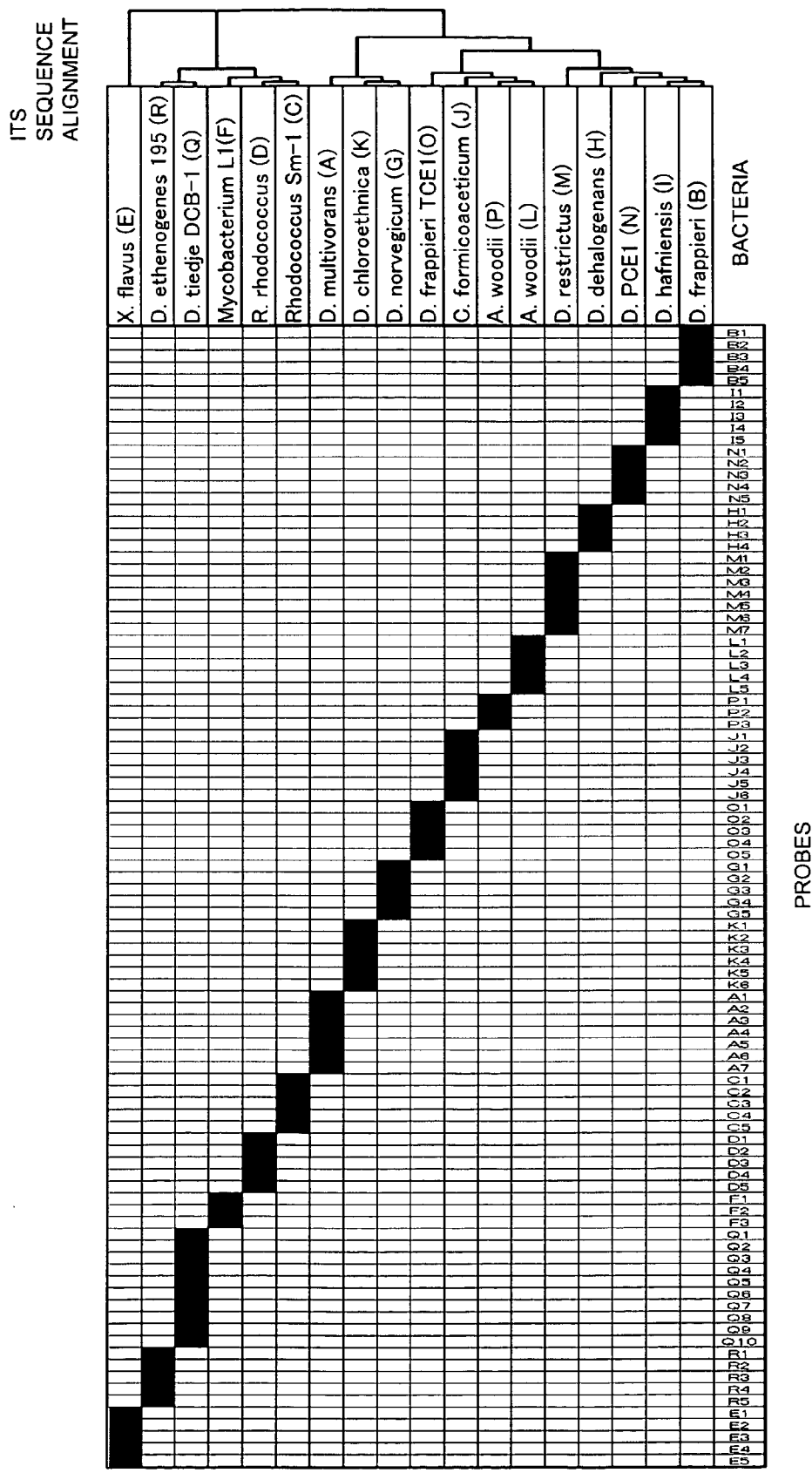
FIG. 1 is a diagram showing results of detection using a DNA microarray performed in Example 1.

Bacteria to be detected in the biological activity judging method according to the present invention are bacteria related to degradation of organochlorine compounds and include one or more types of bacteria among the 18 types denoted as A to R that are currently known to be involved in degradation of PCE into ethene or carbon dioxide. Furthermore, the bacteria related to degradation of organochlorine compounds are not limited thereto and include bacteria that will be identified in the future to be involved in degradation of PCE.

The types of bacteria denoted as A to Q are assigned the following deposit numbers by either of ATCC and DSMZ that are organizations for conservation of living resources and are available from the corresponding one of the organizations.

| A: DSM | 12446 | B: DSM | 13498 | C: ATCC | 51239 |
|---|---|---|---|---|---|
| D: ATCC | 21197 | E: DSM | 10330 | F: DSM | 6695 |
| G: DSM | 1741 | H: DSM | 9161 | I: DSM | 10644 |
| J: ATCC | 27076 | K: DSM | 12431 | L: DSM | 1030 |
| M: DSM | 9455 | N: DSM | 10344 | O: DSM | 12704 |
| P: DSM | 2396 | Q: ATCC | 49306 | | |

PCE is dechlorinated to TCE, then to dichloroethylene (DCE), and further to vinyl chloride (VC), and in a final stage, degraded into ethene or carbon dioxide. FIG. 5A shows a typical degradation route of PCE. Degradation activities of the types of bacteria denoted as A to R with respect to PCE and dechlorinated products thereof have already been known, and the respective biological activities of these types of bacteria are shown in FIG. 5B. Thus, if at least one of the types of bacteria denoted as A to R can be detected in an environment, it can be judged that the environment is provided with a biological activity corresponding to a degradation activity of the at least one of the types of bacteria thus detected.

Concretely, for example, in the case where at least one of the types of bacteria denoted as J, L and P is detected in an environment, it can be judged that the environment has a biological activity of degrading PCE into TCE. Further, in the case where at least one of the types of bacteria denoted as A, G and M is detected, it can be judged that the environment has a biological activity of degrading PCE into cis-dichloroethylene (cisDCE). Further, in the case where at least one of the types of bacteria denoted as B, I, H, N, O and Q is detected, it can be judged that the environment has a biological activity of degrading PCE and TCE into cisDCE. Further, in the case where the bacterium K is detected, it can be judged that the environment has a biological activity of degrading PCE and TCE into DCE. Further, in the case where the bacterium R is detected, it can be judged that the environment has a biological activity of degrading PCE, TCE, DCE and VC into ethene. Further, in the case where at least one of the types of bacteria denoted as C, D and E is detected, it can be judged that the environment has a biological activity of degrading DCE and VC into carbon dioxide. Further, in the case where the bacterium F is detected, it can be judged that the environment has a biological activity of degrading VC into carbon dioxide. Moreover, in the case where two or more types of bacteria that have different degradation activities are detected, it can be judged that the environment has a biological activity as a combination of the respective degradation activities.

A method of detecting a bacterium in the biological activity judging method according to the present invention includes steps of extracting a nucleic acid from an environmental sample and producing a target by a gene amplification method; and hybridizing the target to a DNA probe specific to a bacteria to be detected.

In the present invention, the DNA probe is derived from an ITS region of a bacterium to be detected. That is, a polynucleotide entirely or partly including one of the base sequences represented by SEQ ID NOS: 1 to 18 of the Sequence Listing can be used as the DNA probe in the present invention.

Generally, a 16SrRNA, a 23SrRNA and a 5SrRNA that are ribosomal RNAs (rRNAs) of prokaryotes are transcribed as one transcription unit (operon), and therefore, a 16SrRNA gene and a 23 SrRNA gene are located adjacently on a genome. A region between these genes, i.e. a 16SrRNA gene and a 23SrRNA gene is a so-called 16S-23S Internal Transcribed Spacer (ITS) region.

The inventors of the present invention determined, with respect to the types of bacteria denoted as A to Q, base sequences in the respective ITS regions (assigned SEQ ID NOS: 1 to 17 of the Sequence Listing, respectively) and found for the first time that a polynucleotide having a base sequence within each of these ITS regions can be used to produce a DNA probe unique to each of the types of bacteria denoted as A to Q. The genome base sequence of the bacterium R is determined by Dr. Zinder of Cornell University. Since the base sequence in an ITS region of the bacterium R (SEQ ID NO: 18 of the Sequence Listing) also is specific to the bacterium R, when a DNA probe derived from the ITS region of the bacterium R is used in combination with DNA probes derived respectively from the ITS regions of the 17 types of bacteria denoted as A to Q, the DNA probes can be used as a group of DNA probes that allows all the 18 types of bacteria denoted as A to R to be detected.

As a DNA probe for detecting the types of bacteria denoted as A to R, a DNA probe including a part of an ITS sequence is used more preferably than a DNA probe including the entire ITS sequence. This is because, in general, the sequence specificity of a DNA probe increases with decreasing length of the DNA probe, thus providing improved reliability. Meanwhile, it is necessary that a sequence itself is unique to each of the types of bacteria. A DNA probe has a length of, for example, 10 bases to the entire ITS sequence, and preferably 40 to 80 bases, though there is no limitation thereto.

As a DNA probe for detecting the types of bacteria denoted as A to R, a polynucleotide can be used that is derived from an ITS region and has a length of 40 bases, and a concrete example of such a polynucleotide comprises base sequences represented by SEQ ID NOS: 19 to 115 of the Sequence Listing.

That is, a polynucleotide including one of the base sequences represented by SEQ ID NOS: 19 to 25 of the Sequence Listing can be used as a DNA probe for detecting the bacterium A; a polynucleotide including one of the base sequences represented by SEQ ID NOS: 26 to 30 of the Sequence Listing can be used as a DNA probe for detecting the bacterium B; a polynucleotide including one of the base sequences represented by SEQ ID NOS: 31 to 35 of the Sequence Listing can be used as a DNA probe for detecting the bacterium C; a polynucleotide including one of the base sequences represented by SEQ ID NOS: 36 to 40 of the Sequence Listing can be used as a DNA probe for detecting the bacterium D; a polynucleotide including one of the base sequences represented by SEQ ID NOS: 41 to 45 of the Sequence Listing can be used as a DNA probe for detecting the bacterium E; a polynucleotide including one of the base sequences represented by SEQ ID NOS: 46 to 48 of the Sequence Listing can be used as a DNA probe for detecting the bacterium F: a polynucleotide including one of the base sequences represented by SEQ ID NOS: 49 to 53 of the Sequence Listing can be used as a DNA probe for detecting the bacterium G; a polynucleotide including one of the base sequences represented by SEQ ID NOS: 54 to 57 of the Sequence Listing can be used as a DNA probe for detecting the bacterium H; a polynucleotide including one of the base sequences represented by SEQ ID NOS: 58 to 62 of the Sequence Listing can be used as a DNA probe for detecting the bacterium I; a polynucleotide including one of the base sequences represented by SEQ ID NOS: 63 to 68 of the Sequence Listing can be used as a DNA probe for detecting the bacterium J; a polynucleotide including one of the base sequences represented by SEQ ID NOS: 69 to 74 of the Sequence Listing can be used as a DNA probe for detecting the bacterium K; a polynucleotide including one of the base sequences represented by SEQ ID NOS: 75 to 79 of the Sequence Listing can be used as a DNA probe for detecting the bacterium L; a polynucleotide including one of the base sequences represented by SEQ ID NOS: 80 to 86 of the Sequence Listing can be used as a DNA probe for detecting the bacterium M; a polynucleotide including one of the base sequences represented by SEQ ID NOS: 87 to 91 of the Sequence Listing can be used as a DNA probe for detecting the bacterium N; a polynucleotide including one of the base sequences represented by SEQ ID NOS: 92 to 96 of the Sequence Listing can be used as a DNA probe for detecting the bacterium O; a polynucleotide including one of the base sequences represented by SEQ ID NOS: 97 to 99 of the Sequence Listing can be used as a DNA probe for detecting the bacterium P; a polynucleotide including one of the base sequences represented by SEQ ID NOS: 100 to 105 of the Sequence Listing can be used as a DNA probe for detecting the bacterium Q; a polynucleotide including one of the base sequences represented by SEQ ID NOS: 106 to 115 of the Sequence Listing can be used as a DNA probe for detecting the bacterium R.

With respect to each of the above-described types of polynucleotides comprising the base sequences SEQ ID NOS: 1 to 115 of the Sequence Listing, respectively, even a polynucleotide comprising a base sequence obtained by deletion, substitution or insertion of one to several bases therein can be used as a DNA probe for the biological activity judging method according to the present invention. That is, the DNA probe according to the present invention is a probe containing any one of types of polynucleotides described below in (1) to (4).

(1) A polynucleotide comprising any one of the base sequences represented by SEQ ID NOS: 1 to 115 of the Sequence Listing, respectively.

(2) A polynucleotide comprising a base sequence obtained by deletion, substitution or insertion of one to several bases in the base sequence of the polynucleotide described in (1), which is hybridizable to a polynucleotide comprising a base sequence complementary to the polynucleotide described in (1) under a stringent condition.

(3) A polynucleotide comprising a base sequence obtained by deletion, substitution or insertion of one to several bases in the base sequence of the polynucleotide described in (1), which has a homology of 90% or higher with the polynucleotide described in (1).

(4) A polynucleotide comprising a base sequence complementary to any one of the polynucleotides described in (1) to (3).

The number of bases that can be deleted, substituted or inserted is, for example, as follows. That is, with respect to 40 bases, the number of bases that can be deleted/inserted is 1 to 6, preferably 1 to 3, and more preferably 1 to 2, and the number of bases that can be substituted is 1 to 4, preferably 1 to 2, and more preferably 1. Further, hybridization under a stringent condition means that two DNA fragments are hybridized to each other under a standard hybridization condition as described by Sambrook J. et al. (Expression of cloned genes in *E. coli* (Molecular Cloning: A laboratory manual (1989)) Cold Spring harbor Laboratory Press, New York, USA, 9. 47-9.62 and 11.45-11.61). More concretely, it means that hybridization and washing (for example, in about 2.0×SSC at 50° C.) are performed with reference to ±10° C. of a Tm value. Further, the homology is, for example, 90% or higher, preferably 95% or higher, and more preferably 97.5% or higher.

A gene amplification method for preparing a target to be hybridized to the DNA probe is not limited particularly as long as an ITS region of a bacterium to be detected can be amplified by the method, and as the method, for example, a PCR method can be employed. Since the DNA probe in the present invention is derived from an ITS region of a bacterium, for example, in one gene amplification reaction using a combination of a small number of primers, ITS regions as targets of all the types of bacteria to be detected can be amplified.

For example, the ITS regions of the types of bacteria denoted as A to Q can be amplified by the use of a polynucleotide comprising a base sequence represented by SEQ ID NO: 116 of the Sequence Listing as a sense primer and a polynucleotide comprising a base sequence represented by SEQ ID NO: 117 of the Sequence Listing as an antisense primer. Moreover, in the case of amplifying the ITS region of the bacterium R as well at the same time, a polynucleotide comprising a base sequence represented by SEQ ID NO: 118 of the Sequence Listing as an antisense primer further should be added to a reaction solution.

A detection method by hybridization of a target amplified in the above-described manner to the DNA probe is not limited particularly, and as the method, for example, a conventionally known gene detection technique such as a Southern blotting method, a DNA array method, a DNA microarray method, or a DNA chip method can be used. Among these, a method in which a DNA probe corresponding to a bacterium to be detected is immobilized allows bacteria in all environmental samples to be detected at one time and thus is preferable. Preferably, the target and the DNA probe are labeled suitably depending on the detection method. For example, the target may be labeled at the same time that gene amplification for preparing the target is performed. There is no particular limitation to the labeling, and, for example, fluorescence labeling or RI labeling can be employed.

An environment as a subject of biological activity judgment according to the present invention is not limited particularly and can be, for example, soil, groundwater, pond water, or seawater that is contaminated with at least one of PCE and TCE. A nucleic acid to be used as a template of the target can be extracted from the environmental sample by a conventionally known method such as, for example, using a commercially available nucleic acid extracting kit without any particular limitation. As the nucleic acid, for example, a DNA or a RNA may be used.

A bioremediation method according to the present invention is a method of bioremediation with respect to an environment contaminated with an organochlorine compound that is at least one of PCE and TCE, and includes steps of: performing the method of judging a biological activity in an environment according to the present invention; and stimulating, when a bacterium related to degradation of the organochlorine compound is detected by the method, growth and/or an activity of the bacterium so as to enhance the degradation of the organochlorine compound or a dechlorinated product thereof. In the bioremediation, the capability of an environment to degrade and eliminate an organochlorine compound such as PCE or the like is grasped beforehand by the biological activity judging method according to the present invention, and thus it becomes possible to select a bioremediation method so that the accuracy and promptness of bioremediation can be increased. For example, if the bacterium R is detected, it is expected that PCE can be degraded into ethene using the bacterium R, and thus based on this, biostimulation in which nutrients for enhancing growth and an activity of the bacterium R is introduced into an environment can be selected. Further, for example, similarly in the case where the bacteria K and C are detected, it is expected that PCE can be degraded into carbon dioxide using the two types of bacteria (see FIG. 5B), and thus based on this, biostimulation in which nutrients for enhancing growth and activities of the two types of bacteria are introduced into an environment can be selected.

A bioremediation method according to another aspect of the present invention is a method of bioremediation with respect to an environment contaminated with an organochlorine compound that is at least one of PCE and TCE, and includes steps of: performing the method of judging a biological activity in an environment according to the present invention; and adding at least one of types of bacteria related to degradation of the organochlorine compound other than a detected bacterium to the environment so as to enhance the degradation of the organochlorine compound or a dechlorinated product thereof. For example, in the case where only the bacterium K is detected, the addition of the bacterium C to the environment allows PCE to be degraded into carbon dioxide.

A device for detecting a bacterium according to the present invention is a device that can be used in the biological activity judging method according to the present invention, and includes the DNA probe according to the present invention. The detection device according to the present invention is not limited particularly as long as the device includes the DNA probe that is immobilized and can detect the target hybridized to the DNA probe. In the detection device according to the present invention, preferably, at least two such DNA probes are included, and at least two of the above-described types of bacteria can be detected at the same time. More preferably, the detection device includes a polynucleotide including one of the base sequences represented by SEQ ID NOS: 19 to 115 of the Sequence Listing as a DNA probe and can detect all of the types of bacteria denoted as A to R at the same time.

A DNA microarray according to the present invention is a DNA microarray that can be used in the biological activity judging method according to the present invention, and includes a substrate on which at least one DNA probe according to the present invention is immobilized. In the DNA microarray according to the present invention, preferably, two or more DNA probes according to the present invention are immobilized, and two or more of the above-described types of bacteria can be detected. In order to suppress noise, preferably, the length of the DNA probe(s) immobilized to the DNA microarray according to the present invention is as short as possible, and in order to suppress cross-hybridization by keeping a Tm value constant, preferably, the DNA probes have the same length. There is no particular limitation to the substrate used in the DNA microarray according to the present invention, and as the substrate, a commercially available substrate for a DNA microarray or the like can be used, and the DNA probe(s) can be immobilized to the substrate by a conventionally known method with no particular limitation.

A detecting kit according to the present invention is a kit for detecting a bacterium that can be used in the biological activity judging method according to the present invention, and includes: the DNA probe according to the present invention; and a primer for gene amplification and a reagent for gene amplification that are used for preparing a target to be hybridized to the DNA probe so as to be detected. A kit according to another aspect of the present invention includes the DNA microarray according to the present invention instead of the DNA probe according to the present invention. As the primer for gene amplification, for example, a polynucleotide including the base sequence represented by SEQ ID NO: 116 of the Sequence Listing can be used as a sense primer, and a polynucleotide(s) including the base sequence(s) represented by SEQ ID NO(S): 117 and/or 118 of the Sequence Listing can be used as a antisense primer. As the reagent for gene amplification, a conventionally known reagent such as, for example, a buffer, polymerase, or nucleotide can be used. When necessary, the detection kit according to the present invention may include, for example, a reagent for extracting a nucleic acid and a filter or a chip that are used for preparing a target.

A polynucleotide according to the present invention is a new type of polynucleotide that can be used as a DNA probe for detecting the types of bacteria denoted as A to Q in the biological activity judging method according to the present invention, and is any one of types of polynucleotides described below in (1) to (4). The number of bases to be deleted, substituted or inserted, a stringent condition and a homology are defined in the same manner as in the foregoing description.

(1) A polynucleotide comprising any one of base sequences represented by SEQ ID NOS: 1 to 17 and SEQ ID NOS: 19 to 105 of the Sequence Listing, respectively.

(2) A polynucleotide comprising a base sequence obtained by deletion, substitution or insertion of one to several bases in the base sequence of the polynucleotide described in (1), which is hybridizable to a polynucleotide comprising a base sequence complementary to the polynucleotide described in (1) under a stringent condition.

(3) A polynucleotide comprising a base sequence obtained by deletion, substitution or insertion of one to several bases in the base sequence of the polynucleotide described in (1), which has a homology of 90% or higher with the polynucleotide described in (1).

(4) A polynucleotide comprising a base sequence complementary to any one of the polynucleotides described in (1) to (3).

Hereinafter, the present invention will be described by way of examples.

EXAMPLES

Example 1

Production of a DNA Probe and a DNA Microarray that Allow 18 Types of Bacteria to be Detected at the Same Time 1. Production of DNA Probe A base sequence having 40 bases was designed based on the ITS sequences of the types of bacteria denoted as A to R (assigned SEQ ID NOS: 1 to 18 of the Sequence Listing, respectively) and used as a DNA probe. In designing the DNA probe, a precondition was set that the DNA probe was a single-stranded probe of 40 bases having a GC content of 48 to 50%, exhibited no or almost no complementation, and was not found in the International Nucleotide Sequence Database GenBank (if any, contained two or more mispairs). The following are DNA probes thus produced (of 3 to 10 types for each type of bacterium) and sequence ID numbers of their respective base sequences (SEQ ID NOS: 19 to 115 of the Sequence Listing).

Probes A1 to A7 for the bacterium A have the base sequences represented by SEQ ID NOS: 19 to 25 of the Sequence Listing, respectively; probes B1 to B5 for the bacterium B have the base sequences represented by SEQ ID NOS: 26 to 30 of the Sequence Listing, respectively; probes C1 to C5 for the bacterium C have the base sequences represented by SEQ ID NOS: 31 to 35 of the Sequence Listing, respectively; probes D1 to D5 for the bacterium D have the base sequences represented by SEQ ID NOS: 36 to 40 of the Sequence Listing, respectively; probes E1 to E5 for the bacterium E have the base sequences represented by SEQ ID NOS: 41 to 45 of the Sequence Listing, respectively; probes F1 to F3 for the bacterium F have the base sequences represented by SEQ ID NOS: 46 to 48 of the Sequence Listing, respectively: probes G1 to G5 for the bacterium G have the base sequences represented by SEQ ID NOS: 49 to 53 of the Sequence Listing, respectively; probes H1 to H4 for the bacterium H have the base sequences represented by SEQ ID NOS: 54 to 57 of the Sequence Listing, respectively; probes 11 to 15 for the bacterium I have the base sequences represented by SEQ ID NOS: 58 to 62 of the Sequence Listing, respectively; probes J1 to J6 for the bacterium J have the base sequences represented by SEQ ID NOS: 63 to 68 of the Sequence Listing, respectively; probes K1 to K6 for the bacterium K have the base sequences represented by SEQ ID NOS: 69 to 74 of the Sequence Listing, respectively; probes L1 to L5 for the bacterium L have the base sequences represented by SEQ ID NOS: 75 to 79 of the Sequence Listing, respectively; probes M1 to M7 for the bacterium M have the base sequences represented by SEQ ID NOS: 80 to 86 of the Sequence Listing, respectively; probes N1 to N5 for the bacterium N have the base sequences represented by SEQ ID NOS: 87 to 91 of the Sequence Listing, respectively; probes O1 to O5 for the bacterium O have the base sequences represented by SEQ ID NOS: 92 to 96 of the Sequence Listing, respectively; probes P1 to P3 for the bacterium P have the base sequences represented by SEQ ID NOS: 97 to 99 of the Sequence Listing, respectively; probes Q1 to Q6 for the bacterium Q have the base sequences represented by SEQ ID NOS: 100 to 105 of the Sequence Listing, respectively; probes R1 to R10 for the bacterium R have the base sequences represented by SEQ ID NOS: 106 to 115 of the Sequence Listing, respectively.

2. Production of DNA Microarray and Confirmation of Specificity of DNA Probe

Next, using an Affymetrix 417 Arrayer (manufactured by Affymetrix, Inc.), each of the above-described 97 types of DNA probes was printed in a customized manner on a TaKaRa-Hubble Slide Glass (manufactured by Takara Bio Inc.) to produce a DNA microarray. Then, a target was prepared using each of the types of bacteria denoted as A to R and hybridized to the DNA microarray so as to be used to confirm the specificity of the DNA probes.

The target was prepared in a manner that an ITS region of each of the above-described types of bacteria was amplified by a PCR method. In performing the PCR, as a sense primer, a non-labeled primer having the base sequence represented by SEQ ID NO: 116 of the Sequence Listing was used. Further, as an antisense primer, a Cy3-labeled primer having the base sequence represented by SEQ ID NO: 117 of the Sequence Listing was used for the bacteria other than the bacterium R, and a Cy3-labeled primer having the base sequence represented by SEQ ID NO: 118 of the Sequence Listing was used for the bacterium R. Reaction conditions for the PCR were set so as to conform to a standard protocol.

An amplified product to be used as a target resulting from the PCR was desalted using an AutoSeq G-50 (manufactured by Pharmacia Corporation), then vacuum-dried using a SpeedVac (manufactured by Savant Instrument, Inc.) and then dissolved in a buffer of 5×SSC, 0.2% SDS and 50% formamide at their respective final concentrations. A target solution thus obtained was boiled at a temperature of 94° C. for 3 minutes, then cooled with ice for at least two minutes, and then applied on the DNA microarray. The DNA microarray was covered with a cover glass and then placed in a hybridization chamber at a set temperature of 42° C. for at least 4 hours. After that, the DNA microarray was washed with 0.2×SSC and 0.2% SDS for 5 minutes, with 0.2×SSC for 5 minutes, and with 0.05×SSC for several seconds, and then spin-dried at a speed of 1,800 rpm. Scanning was performed using a ScanArray version 5 (manufactured by PerkinElmer Japan Co., Ltd.) to obtain measurement results.

The results are shown in FIG. 1. FIG. 1 is a graph showing whether the targets derived from the respective ITS sequences of the 18 types of bacteria denoted as A to R plotted on a vertical axis were hybridized to the 97 DNA probes plotted on a horizontal axis. In the figure, black-painted portions show that the DNA probes were hybridized to the targets, respectively exhibiting fluorescent signals of 500 fluorescent units or more. A phylogenetic tree on the vertical axis was created based on the alignment of the ITS sequences. As shown in FIG. 1, it was proved that the targets prepared using the types of bacteria denoted as A to R were hybridized significantly only to the DNA probes for the types of bacteria denoted as A to R, respectively, without being cross-hybridized.

Example 2

Judgment 1 of Biological Activity in Contaminated Environment

Using a FastPrep bead-beater and a soil DNA extraction kit (manufactured by Qbiogene, Inc.) and following instruction manuals, a DNA was extracted from 250 mg of a soil sample provided by Matsushita Environmental & Air-conditioning Engineering. The DNA in an amount of about 1 µl was added to 50 µl of a standard Amplitaq Gold PCR mixture (manufactured by Applied Biosystems) containing a non-labeled sense primer 27F (SEQ ID NO: 116 of the Sequence Listing) and a Cy3-labeled antisense primer 132 R (SEQ ID NO: 117 of the Sequence Listing) or 341R (SEQ ID NO: 118 of the Sequence Listing). After performing PCR in accordance with a standard protocol, a PCR amplified product was desalted using an Autoseq G-50 (manufactured by Pharmacia Corporation) and then vacuum-dried using a SpeedVac (manufactured by Savant Instrument, Inc.). The PCR amplified product thus dried was dissolved in a buffer of 5×SSC, 0.2% SDS and 50% formamide at their respective final concentrations, and a solution thus obtained was boiled at a temperature of 94° C. for 3 minutes, then cooled with ice for at least two minutes, and then applied on the DNA microarray produced in Example 1. The DNA microarray was covered with a cover glass and then placed in a hybridization chamber at a set temperature of 42° C. for at least 4 hours. After that, the DNA microarray was washed with 0.2×SSC and 0.2% SDS for 5 minutes, with 0.2×SSC for 5 minutes, and with 0.05×SSC for several seconds, and then spin-dried at a speed of 1,800 rpm. Scanning was performed using a ScanArray version 5 (manufactured by PerkinElmer Japan Co., Ltd.) to obtain measurement results.

Figure 2A:
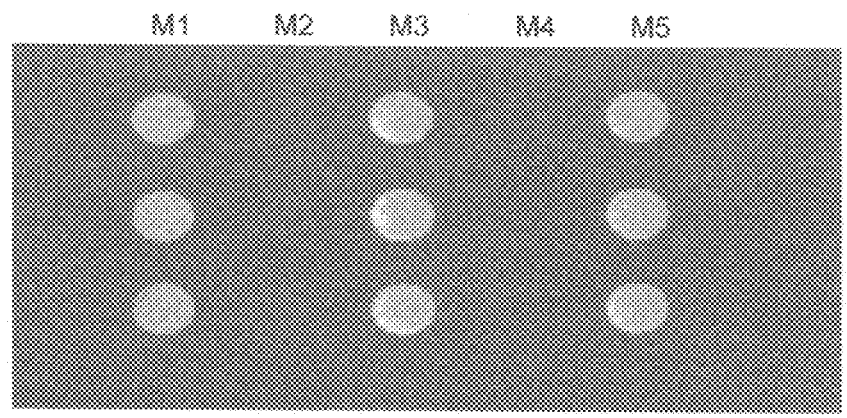
FIG. 2A is a photograph showing results of scanning a DNA microarray in Example 2.
Figure 2B:
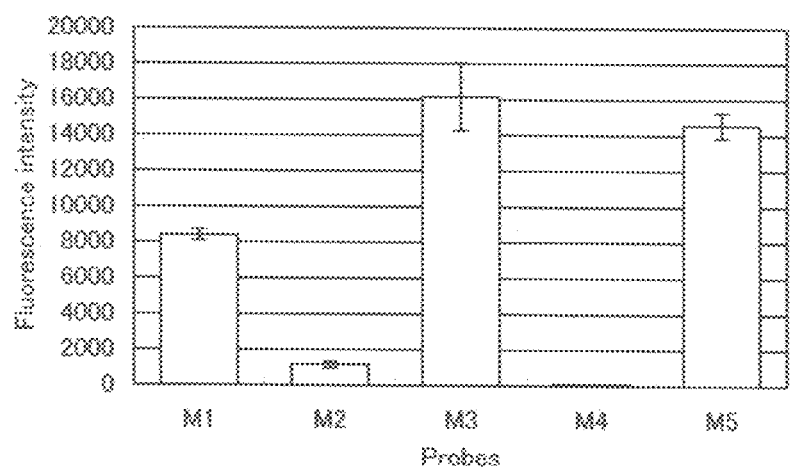
FIG. 2B is a graph showing a result of detecting a bacterium M using the DNA microarray in Example 2.

The results of the scanning of the DNA microarrays are shown partially in FIG. 2. FIG. 2A shows scan images, and FIG. 2B is a graph in which the results are shown quantitatively. As shown in FIG. 2, significant hybridization of the bacterium M (*Dehalobacter restrictus* DSM 945) to the probes was detected. Thus, it could be judged that the soil as the sample had capability to degrade PCE into cisDCE (See FIG. 5B).

Example 3

Judgment 2 of Biological Activity in Contaminated Environment

In this example, 300 ml of a groundwater sample provided by Matsushita Environmental & Air-conditioning Engineering was used instead of the soil sample, and a DNA was extracted from debris obtained by centrifugation at a speed of 7,000 rpm with respect to the groundwater sample. Except for this, in the same manner as in Example 2, bacteria in the groundwater sample were detected using the DNA microarray.

Figure 3A:
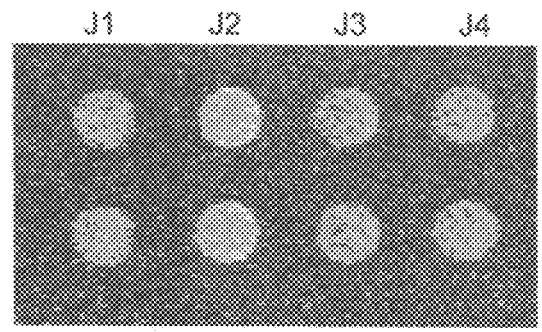
FIG. 3A is a photograph showing results of scanning a DNA microarray in Example 3.
Figure 3B:
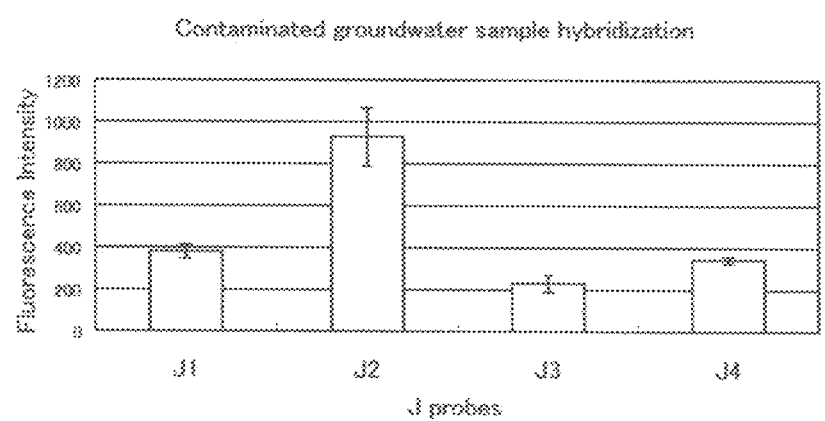
FIG. 3B is a graph showing a result of detecting a bacterium J using the DNA microarray in Example 3.

The results of the detection are shown partially in FIG. 3. FIG. 3A shows scan images, and FIG. 3B is a graph in which the results are shown quantitatively. As shown in FIG. 3, significant hybridization of the bacterium J (*Clostridium formicoaceticum* ATCC 27076) to the probes was detected. Thus, it could be judged that the soil as the sample had the capability to degrade PCE into TCE (See FIG. 5B).

Example 4

Judgment 3 of Biological Activity in Contaminated Environment

In this example, an anaerobic enrichment culture sample provided by Dr. T. H. Lee (the Republic of Korea) was used instead of the soil sample. Except for this, in the same manner as in Example 2, the bacteria in the sample were detected.

Figure 4:
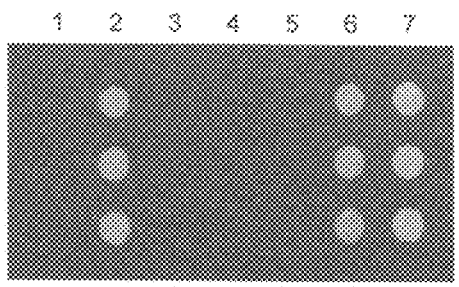
FIG. 4 shows photographs showing results of scanning a DNA microarray in Example 4, in which bacteria A, B, I, J, M, N and O were detected, respectively.
Figure 4:
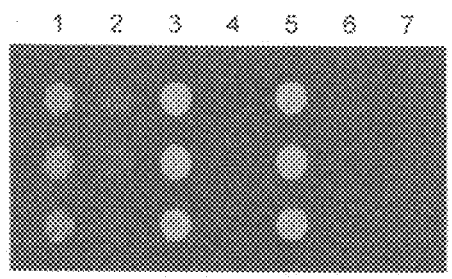
Figure 4:
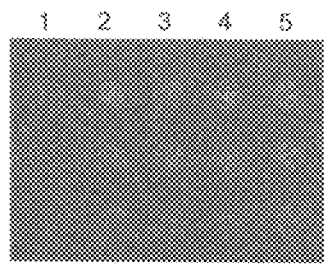
Figure 4:
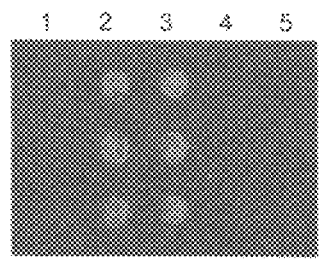
Figure 4:
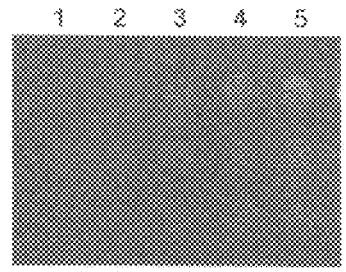
Figure 4:
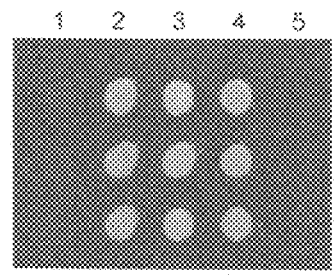
Figure 4:
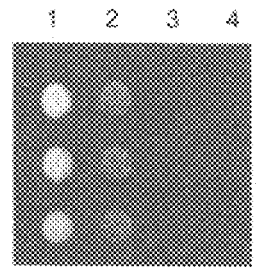

Results of the detection are shown in FIG. 4. As shown in FIG. 4, strong signals were detected in part of the probes for the bacteria A, J, M, N and O, and weak signals were detected also in the probes for the bacteria B and J. Thus, it could be judged that the sample had capability to convert PCE into cisDCE (see FIG. 5B). These judgment results agreed with the analysis data on PCE/cisDCE in the enrichment culture provided by Dr. T. H. Lee.

INDUSTRIAL APPLICABILITY

As described in the foregoing discussion, the method of judging a biological activity in an environment according to the present invention and the polynucleotide according to the present invention are useful in the method of remedying an environment contaminated with PCE or the like, particularly, in the field of bioremediation.

Sequence Listing Free Text

SEQ ID NO: 116 Sense primer 27F for PCR

SEQ ID NO: 117 Antisense primer 132R for PCR

SEQ ID NO: 118 Antisense primer 341R for PCR

The invention claimed is:

1. A method of judging a biological activity in an environment contaminated with an organochlorine compound that is at least one of tetrachloroethylene (PCE) and trichloroethylene (TCE), the method comprising:

amplifying a nucleic acid extracted from an environmental sample by a gene amplification method so as to use the amplified product as a target; hybridizing the target to a DNA probe including a base sequence unique to each of 17 types of anaerobic bacteria denoted below as A to Q, which are related to degradation of the organochlorine compound, in an attempt to detect the 17 types of bacteria in the environment; and judging capability of the environment to eliminate the organochlorine compound based on degrading capability of the each of 17 types of bacteria that is detected with respect to the organochlorine compound and a dechlorinated product thereof, wherein the DNA probe is a combination of 87 types of DNA probes consisting of SEQ ID NOS: 19 to 105 or the complement of SEQ. ID NOS: 19-105, wherein each of the probe is bonded specifically to an internal transcribed spacer region of any one of the 17 types of bacteria denoted below as A to Q without occurrence of cross-hybridization, A: *Dehalospirillum multivorans* B: *Desulfitobacterium frappieri* C: Actinomycetales Sm-1 (*Rhodococcus* sp. Sm-1) D: *Rhodococcus rhodococcus* E: *Xanthobacter flavus* F: *Mycobacterium* L1G: *Desulfomicrobium norvegicum* (*Desulfovibrio baculatus*) H: *Desulfitobacterium dehalogenans* I: *Desulfitobacterium hafniense* J: *Clostridium formicoaceticum* K: *Desulfuromonas chloroethenica* L: *Acetobacterium woodii* DSM 1030 M: *Dehalobacter restrictus* N: *Desulfitobacterium* sp. strain PCE1 O: *Desulfitobacterium frappieri* TCE1 P: *Acetobacterium woodii* DSM 2396 Q: *Desulfomonile tiedjei* DCB-1.

2. The method according to claim 1, wherein the gene amplification method with respect to the nucleic acid uses as a sense primer, a primer that contains a polynucleotide comprising a base sequence represented by SEQ ID NO: 116 of the Sequence Listing, and as an antisense primer, a primer that contains a polynucleotide comprising a base sequence represented by SEQ ID NO: 117 of the Sequence Listing.

3. The method according to claim 1, wherein the contaminated environment is selected from a group consisting of soil, groundwater, pond water and seawater.

* * * * *

```
                        SEQUENCE LISTING

<160> NUMBER OF SEQ ID NOS: 118

<210> SEQ ID NO 1
<211> LENGTH: 742
<212> TYPE: DNA
<213> ORGANISM: Dehalospirillum multivorans

<400> SEQUENCE: 1
aagtcgtaac aaggtaaccg taggagaacc tgcggttgga tcacctcctt tctagagtat      60 agggcacta tctcacaatg gtgctccggc gagcatagct agggaagctt atttagtttt     120
gagagattga atgaaaaagg ggcttatagc tcaggtggtt agagcgtacc cctgataagg     180
gtaaggtcag aggttcgagt cctcttaagc ccaccatggg gaattagctc agctgggaga     240
gcgcctgctt tgcacgcagg aggtcagcgg ttcgatcccg ctattctcca ccattttta      300 gagaaatggt gaaagattgc caagagacat tgttagtgag aatgaagaca caatgtctaa     360
tataagaaca atttaggttg tttttatatt agactttta gtctaagttt atgttctaca      420
atttagaata cgacgctttg tgttgtgctg taggtttggt tctttaagat agctttgcta     480
tctggtgaaa gaacataaag atgttattta atttattatt gtcaaagtca acaaaacgca     540
aaaaaaacaa tttacaactt gttagatgtt ttacatttaa taagggagtg aaatgtgcat     600
tagaatacaa ataggtaagc tattaagagc gaatggtgga tgcctaggct gtaagaggcg     660
atgaaggacg tactagactg cgataagtta cggggagctg tcaagaagct ttgatccgta     720
aatttccgaa tggggcaacc ca                                              742

<210> SEQ ID NO 2
<211> LENGTH: 527
<212> TYPE: DNA
<213> ORGANISM: Desulfitobacterium frappieri

<400> SEQUENCE: 2
aagtcgtaac aaggtagccg tatcggaagg tgcggctgga tcacctcctt tctaaggaga      60
catgttcact ctggaagtga gcatatccta aggtcgatgc tttgaaggac gtcacggaag     120
agatgaagtg aaacggttca aagctggaga agtctgaaga gacttcgaaa tgccgaagag     180
gcaaagcagg ggaaatctgc ataagatgac cctgaaatcg agtcaaacct gttcaagcgc     240
aagcttactt gttgtttagt tttgagggac cagcaatgga aactcattat tttttgacc      300 aaaagtcaag aaaaactgtt ctttgaaaac tgcacagaga agaaaaaact gtaatttagg     360
ataacatctg aaaaacctga atgtggcgga gacgtttggt caagctacta agggcgtacg     420
```

| | |
|---|---|
| gtggatgcct aggcgctaag agtcgaagaa ggacgcggcg agcggcgaaa cgccacgggg | 480 |
| agcagtaagc atgctttgat ccgtggatat ccgaatgggg caaccca | 527 |

<210> SEQ ID NO 3
<211> LENGTH: 478
<212> TYPE: DNA
<213> ORGANISM: Actinomycetales Sm-1

<400> SEQUENCE: 3

| | |
|---|---|
| aagtcgtaac aaggtagccg taccggaagg tgcggctgga tcacctcctt tctaaggagc | 60 |
| aactcccgtc ggtgggtcac acaggtgact ccgccacggg cagagccatt tcggattcac | 120 |
| acgtaatccg gtggtgctca tgggtggaac gctgacagct acttctcgtc cgggtcccgt | 180 |
| ttctgtgcgg gatccgagga gttatatcgg tgcactgttg ggtcctgaga gaacacgcga | 240 |
| gtgttttgtc agcgacgatg atccgcgaaa caagaggaca tggttttctt gcggtagggg | 300 |
| ttgttgtgtg ttgtttgaga actgcacagt ggacgcgagc atctttgttg taagtgttta | 360 |
| tgagcgtacg gtggatgcct tggcaccagg agccgatgaa ggacgtggga ggctgcgata | 420 |
| tgcctcgggg agctgtcaac cgagctgtga tccgaggatt ccgaatggg gcaaccca | 478 |

<210> SEQ ID NO 4
<211> LENGTH: 478
<212> TYPE: DNA
<213> ORGANISM: Rhodococcus rhodococcus

<400> SEQUENCE: 4

| | |
|---|---|
| aagtcgtaac aaggtagccg taccggaagg tgcggctgga tcacctcctt tctaaggagc | 60 |
| aactccttgc tcggaccagc acacaggtgc cgggggagcg aggcagagcc atttcggatt | 120 |
| cacacgtaat ccgtggtgc tcatgggtgg aacgctgaca gtcatcaccg cgcgggaagg | 180 |
| acccgagtgt ccttctgcgg tggttatatc ggtgcactgt gggtcctga gagaacacgc | 240 |
| gagtgttttg tcagcgacga tgatcgggaa cgaaggggtt gtttcttctt ccggtaccgg | 300 |
| ttgttgtgtg ttgtttgaga actgcacagt ggacgcgagc atctttgttg taagtgttta | 360 |
| tgagcgtacg gtggatgcct tggcaccagg agccgatgaa ggacgtggga ggctgcgata | 420 |
| tgcctcgggg agctgtcaac cgagctgtga tccgaggatt ccgaatggg gaaaccca | 478 |

<210> SEQ ID NO 5
<211> LENGTH: 952
<212> TYPE: DNA
<213> ORGANISM: Xanthobacter flavus

<400> SEQUENCE: 5

| | |
|---|---|
| aagtcgtaac aaggtagccg taggggaacc tgcggctgga tcacctcctt tctaaggacg | 60 |
| atccctcagt attgagactt cggtctcgat ctatcggatc tcttcagaaa catcagccgg | 120 |
| acataggtga aaacatcatg atctggcatt ggcgggacac cgccgtcttc gtttctcttt | 180 |
| cttcgcggac aagcttgacg cccaggttgc ggtcctttgg actgcgttcc ggtttcgggc | 240 |
| ctgtagctca ggtggttaga gcgcacccct gataagggtg aggtcggacg ttcgagtcgt | 300 |
| cccaggccca ccaccatcag acagttcttg cctgcgcctc atgtccgaag cttcgcgaac | 360 |
| tctcgcctgt ggcatcctgt gatgggccha tagctcagtt gggagagcgc gtgctttgca | 420 |
| agcatgaggt cgtcggttcg atcccgtctg ctccaccat tcttctttc ttgaggaaga | 480 |
| tgatggcagg gtggtttgcg ctcggctcct ttgagtgaag gctcttgggg tcttgagcgt | 540 |
| cttgtccgcg aatatctgtt tcgcatgttc catcatgccg gtcteeggcg gaacatgcac | 600 |

```
ggctgtatga catcgtgaat agggcattga tcgactgtac cgtggcaaca cggtcgggtc        660
gtggggaagg tggcgacacc tttcgatgcg atcattgggt gctgaccgca ccattgtcga        720
caatgcgaag ctggtctttt caaagaagac gtcgaagccg tccggccggg agcaatcctg        780
gtgcgggcct ctgccgaggg gtgggcatcg acgatgagaa cgatcaagtg tcttaagggc        840
attcggtgga tgccttggcg ctaagagcg aagaaggacg tgatacgctg cgataagctt        900
cggggagccg cgaatgggct tgatccgga gatttccgaa tggggcaacc ca                952

<210> SEQ ID NO 6
<211> LENGTH: 579
<212> TYPE: DNA
<213> ORGANISM: Mycobacterium L1

<400> SEQUENCE: 6
aagtcgtaac aaggtagccg taccgaaggt gcggctggat cacctccttt ctaaggagca         60
ccacgagacc tggccggccc gtaaatcgcg ggatcagccg attgtcaggc gattcgttgg        120
atggcccttt cacctgtagt gggtgggggt ctggtgcacg acaagcaaac gaccaggatg        180
gggaccttcc ttgtgggggt tgtctggtgc tgccaaacac actgttgggc tttgagacaa        240
caggcccgtg cccgggtttc cgggtggctc cgcggtggtg gggtcggcgt gttgttgcct        300
cactttggtg gtggggtgtg gtgtttgatt tgtggatagt ggttgcgagc atctagcacg        360
caaatgtggc tctcgaggct ttcggtctg ggggtgtgt ttgtgtgctt ttgatgtgca        420
gtttcttttt tcgaattggt tttttgtgtt gtaagtgttt aagggcgcat ggtggatgcc        480
ttggcactgg gagccgatga aggacgtggg aggctgcgtt atgcctcggg gagctgtcaa        540
ccgagcgtgg atccgaggat gtccgaatgg ggcaaccca                              579

<210> SEQ ID NO 7
<211> LENGTH: 523
<212> TYPE: DNA
<213> ORGANISM: Desulfomicrobium norvegicum

<400> SEQUENCE: 7
aagtcgtaac aaggtagccg tagggggaacc tgcggctgga tcacctcctt atcaagaatt         60
ctccaactcg ctatttactt gcaaggtttc ttaccttgtc ggtttagaaa tgggcttgta        120
gctcaggtgg ttagagcgca cgcctgataa gcgtgaggtc ggaagttcaa gtcttcccag        180
gcccaccatt tcttagtggg ggtgtagctc agctgggaga gcgcctgcct tgcacgcagg        240
aggtcatcag ttcgatcctg ttcacctcca ccattttcca actcgacaag aatttatgtt        300
gctagtcttt atcgtcagag tgtcttttga cactatggcg cccaagcata gcagcttgtg        360
atcattgaca gacgaatagg tgaagagaag agagttaaga tgttaagggc atacggtgga        420
tgccttggcg tcaggaggcg atgaaggacg tggaaggctg cgataagcct cggggagccg        480
tcaagcaggc tttgatccgg ggatttccga atggggcaac cca                         523

<210> SEQ ID NO 8
<211> LENGTH: 662
<212> TYPE: DNA
<213> ORGANISM: Desulfitobacterium dehalogenans

<400> SEQUENCE: 8
aagtcgtaac aaggtagccg tatcggaagg tgcggctgga tcacctcctt tctaaggaga         60
catggtttct cgctagagaa atcatatcct aaggtcgatg ctttgaagaa cgtcacggaa        120
```

```
gcaatgaagt gaaacgattc aaagtcggag aagtcttaag agacttctta taggaaactt      180
ggcttgtgtg aagcatgagc agaagccata gttgacttat ccacggagtg gaaaaatgcc      240
gaagaggcaa acggagcaa tccgtaaagt atgggaaatg aagctgttga agttaaaagc       300
taacttgttg tttagttttg agggaccata agtcttcta tatgggggta tagctcagct       360
gggagagcac ctgccttgca agcagggggt cagcggttcg atcccgctta cctccaccat      420
aatatatctg gtttctctaa tgtttattat gttctttgaa aactgcacag agaagaagaa      480
aactgtaatt aggataacat ctaaaaccta gaagtggcgg caaaaaacgt ttggtcaagc      540
tactaagggc gtacggtgga tgcctaggcg ctaagagtcg aagaaggacg cggcgagcgg      600
cgaaacgcca cggggagcag taagcatgcc ttgatccgtg gatatccgaa tggggcaacc      660
ca                                                                     662

<210> SEQ ID NO 9
<211> LENGTH: 775
<212> TYPE: DNA
<213> ORGANISM: Desulfitobacterium hafniense

<400> SEQUENCE: 9
aagtcgtaac aaggtagccg tatcggaagg tgcggctgga tcacctcctt tctaaggagc       60
catgttcact ctggaagtga gcatatccta aggtcgatgc tttgaaggac gtcacggaag      120
agatgaagtg aaacggttca agctggaga agtctataga gacttcgaag tgccgaagag      180
gcaaagcagg ggaaatctgc ataagatgac cctgaagtcg agtcaaacct gttcaagcgc      240
aagcttactt gttgtttagt tttgagagac cataaagtct tctatgggct tatagctcag      300
ctggttagag cgcacgcctg ataagcgtga ggtcggtggt tcgagtccac ctaggcccac      360
cattattcaa agaggataga gacccgaacc tccaaacaat acttcacgcc agaacatacc      420
taacaggggt gagtattgag aggggagcgg ctcccctctc aacgacatgg gggtatagct      480
cagctggggg agcacctgcc ttgcaagcag ggggtcagcg gttcgatccc gcttacctcc      540
accatcatat actggtttct ctaatgttct ttgaaaactg cacagagaag aaaaaactgt      600
aatttaggat aacatctgaa aaacctgaat gtggcggaga cggttggtca agctactaag      660
ggcgtacggt ggatgcctag cgcctaagag tcgaagaagg acgcggcgag cggcgaaacg      720
ccacggggag cagtaagcat gccttgatcc gtggatatcc gaatgggca accca            775

<210> SEQ ID NO 10
<211> LENGTH: 422
<212> TYPE: DNA
<213> ORGANISM: Clostridium formicoaceticum

<400> SEQUENCE: 10
aagtcgtaac aaggtagccg tatcggaagg tgcggctgga tcacctcctt tctaaggaga       60 aaggcttta ctatactgtt taattttgag ggacttttgt ttctcaataa gcagacaacc      120
aaaatcttag attttgtgtt agtcgcttag ttaaaaattc tgtaattcac gacaatagtt      180
ttaaaccaac aaaaaatgaa tggaagaatt tttaacatct atagtctttt agattgttct      240
ttgaaaacta acaatgata tgagaaaaga aaagctgaag taattcacta aaggtcaagt       300
tattaagggc aaaggtgga tgccttggca ctaggagccg aagaaggacg tggtaagctg       360
cgaaaagcca cggggagctg caagcaagta ttgatccgtg gatgtccgaa tggggaaacc      420
ca                                                                     422
```

<210> SEQ ID NO 11
<211> LENGTH: 699
<212> TYPE: DNA
<213> ORGANISM: Desulfuromonas chloroethenica

<400> SEQUENCE: 11

```
aagtcgtaac aaggtagccg taggggaacc tgcggcctgg atcacctcct ttctaaggag        60
cctccttact cgtaagagta aaggcatcct ggtcaatccc tcggcatggt ccgagcggat       120
gcccgcaaag catcattgtc tgctatttag ttttgagaga ccagaacctc gcaagaggtt       180
ttttgttctt tgagacaaga cgaacgaagg tggaagtggg ctagtagctc agctggctag       240
agcacacgac tgataatcgt gaggtcggag gttcgagtcc tccctggccc accagattat       300
ttggggtgt agctcagttg ggagagcgcc tgccttgcac gcaggaggtc atcggttcga       360
tcccgttcac ctccaccaga tgttctgtca ggagtaagga gagaagagtg aggagtacac       420
ctcaccctaa cgccttacgc ctcaccgatt tccttgttct ttggcaattg cataagactg       480
atacgatgca cgaagtaaag cgttgcgtac gcaagtacgt gacacgcgaa ggtagcaaca       540
cgatcgctta gtagaagac ttttttatgg tcaagctatt aagggcgtac ggtggatgcc       600
ttggcatcgg gaggcgatga aggacgtggt aagctgcgaa aagcttcggt aagccgctaa       660
acaggctttg acccggagat gtccgaatgg ggaaaccca                              699
```

<210> SEQ ID NO 12
<211> LENGTH: 391
<212> TYPE: DNA
<213> ORGANISM: Acetobacterium woodii

<400> SEQUENCE: 12

```
aagtcgtaac aaggtagccg tatcggaagg tgcggctgga tcacctcctt tctagggaat        60
acaggaagtc atggtactat tttcttttgt atgaccatct ggttatgcaa aaacagttaa       120
agaaggcatc ttaggatgca ttttttaacg ggacaaatac cggagtagtg gtagcaggtc       180
ccaatcgatc attgaaaaca gcatagtgta taaataaaat tataaaatac aatttcttaa       240
cacgaaaacg taaattatta ggatcaagaa gaaaagagca cagggtgaat gccttggcaa       300
tcagagccga cgaaggacgc gacaagctgc gaaaagctac gtgtaggtgc ataaccgt        360
taaagcgtag atatccgaat ggggcaaccc a                                      391
```

<210> SEQ ID NO 13
<211> LENGTH: 608
<212> TYPE: DNA
<213> ORGANISM: Dehalobacter restrictus

<400> SEQUENCE: 13

```
aagtcgtaac aaggtagccg tatcggaagg tgcggctgga tcacctcctt tctaaggaga        60
accgattgaa gctagacttc aatctactcc aaggtcggta cttagagtaa agcagtgcaa       120
actggactga ctctcaagta aggtgagttt agcaatttat ttcttgttgt ttagttttga       180
gtgacctgag cacagtaatg tgtaaaagaa acactcaaat aatgtccata catatcagag       240
attctggtaa gtatggaaaa acatccttgt tctttgaaaa ctgcacaacg agaaaagcag       300
aatgcgaaat gcgaaagtaa agacaacgaa atggcgttca aattctaaag cgcaaaaact       360
taacgtttc gcgcgtggca aatttgaact taggagcatc tatgctccgt caggtaagaa       420
ttactaagcg cataggagac attcaaatca tctataacaa gtcgaggaag aaccagaagg       480
tcaagatata aagggcatac ggtggatgcc ttggcgccaa gagccgaaga aggacgcggt       540
```

```
taacagcgaa atgccacggg gagtcgtaag caggcataga tccgtggatg tccgaatggg      600
gaaaccca                                                              608

<210> SEQ ID NO 14
<211> LENGTH: 689
<212> TYPE: DNA
<213> ORGANISM: Desulfitobacterium sp. strain PCE1

<400> SEQUENCE: 14
aagtcgtaac aaggtagccg tatcggaagg tgcggctgga tcacctcctt tctaaggaga      60 catggttct  cgctagagaa atcatatcct aaggtcgatg ctttgaagga cgtcatggaa     120
gcaatgaagt gaaacgattc aaagttggag aagtcttaag agacttctga agccgaaga     180 ggcaaaacgg agcaatccgt aaagtatgag aaatgaagct gttgaagtta aaagctaact     240
tgttgtttag ttttgaggga ccataaagtc ttctatgggc ttatagctca gctggttaga     300
gcgcacgcct gataagcgtg aggtcggtgg ttcgagtcca cctaggccca ccataaaaga     360
ttgatattgt gggggtatag ctcagctggg agagcacctg ccttgcaagc aggggggtcag    420 cggttcgacc ccgcttacct ccaccataat atatctggtt tctctaatgt ttattatgtt     480
ctttgaaaac tgcacagaga agaagaaaac tgtaattagg ataacatcta aaacctagaa     540
gtggcggcaa aaacgtttg gtcaagctac taagggcgta cggtggatgc ctaggcgcta     600
agagtcgaag aaggacgcgg cgagcggcga acgccacgg ggagcagtaa gcatgccttg     660
atccgtggat atccgaatgg ggcaaccca                                       689

<210> SEQ ID NO 15
<211> LENGTH: 468
<212> TYPE: DNA
<213> ORGANISM: Desulfitobacterium frappieri TCE1

<400> SEQUENCE: 15
aagtcgtaac aaggtagccg tatcggaagg tgcggctgga tcacctcctt tctaaggagt      60
tcataaggac tcacactgtt ttgtttataa atttgattcg ctgaatttcc agaatcaatc     120
acattgaaat cctttggatt tcaattgtta attgtgcact gtgaaatgcg aattgataac     180 gtggggtgt agctcagttg ggagagcacc tgccttgcaa gcaggggtc aggagttcga      240 ctctcctcat ctccaccaaa gacattcata gtttaaatta attatgaatt gtttaaactg     300
aacattgaaa actacaaata tacaataaac atgaaatagg tcaagttatt aagggcgtag     360
ggcgaatgcc ttggcaccaa gagccgatga aggacgggat aagcaccgat atgcttcggg     420
gagtcgcaaa tagacattga tccggagatt tccgaatggg gcaaccca                 468

<210> SEQ ID NO 16
<211> LENGTH: 511
<212> TYPE: DNA
<213> ORGANISM: Acetobacterium woodii

<400> SEQUENCE: 16
aagtcgtaac aaggtagccg tatcggaagg tgcggctgga tcacctcctt tctaaggaaa      60
acagggagtc atggtactat tttcttttgt atgacctta ggttatacaa aaggatcgta      120
gtttctggca attttcttta ttttataaa gatgaaaatt gacataaact gcgttagttt      180
ttacaccgct catgcgctaa cgcttaatga gctgccaaat tgaaaatttg ggtaaaaacg     240
tcaaagtggt cattgaaaac agcatagtgt attaaaaaaa catacaattt cagatgttaa     300
caacataaga aaaacgtaag ttaaaggatc gtagttttag gactacaggc gactgacgaa     360
```

```
gttctactgt cagttgttaa ggatcaagaa atgaagggca cagggcggat gccttggcac      420
tcagagccga tgaaggacgc gacaagctgc gaaaagctgc gtgaaggtgc acataaccgt      480
tgaagcgcag atatccgaat ggggcaaccc a                                     511

<210> SEQ ID NO 17
<211> LENGTH: 471
<212> TYPE: DNA
<213> ORGANISM: Desulfomonile tiedjei DCB-1

<400> SEQUENCE: 17
aagtcgtaac aaggtagccg taggggaacc tgcggctgga tcacctcctt tctaaggtgt       60
aaccttagta tccgaacgca cacatctgct attcagttct gagaggttga cgataacggc      120
ttcgggccta tagctcagtt cggttagagc gcacgcctga taagcgtgag gtcgttggtt      180
caattccaac taggcccacc acgcctctat cggggtgta gctcagctgg gagagcacct       240
gctttgcaag caggggtca tcggttcgaa tccgttcacc tccaccagtt ctttgacaat       300
cgaataggtt ttagatcgag gatactcata tatttaggca atcaagctac taagggccta      360
cggtggatgc cttggcatcg aagacgatg aaggacgtgg ttagctgcga taagcctcgg       420
ggagttgcta aacacactgt gatccgggga tttccgaatg gggcaaccca a               471

<210> SEQ ID NO 18
<211> LENGTH: 847
<212> TYPE: DNA
<213> ORGANISM: Dehalococcoides ethenogenes 195

<400> SEQUENCE: 18
ggactggtaa ttgggacgaa gtcgtaacaa ggtagccgta gcggaagctg cggctggatc       60
acctcctttc taaggataat tggcctcgtg cctattaacc taggtcgata tccgacttaa      120
aacggatact tctcttttct ttccgctatc caggggttaa ggtgttagtg ttataagggg      180
ataaaaatta cttctcctg attgctaacc tgtatctatc ccgctttgaa actcatgtag       240
gttttgttag gcattttggg ctgaaggact tgcgctaagc gtcctgtttg ctatattata      300
ttgacgtttt tcgggtagta tttcgaagat acccaatctg tctgttgtta tcaatcgggc      360
cattagctca gctggttaga gcgcagtcct gataagactg aggtccttgg ttcgagacca      420
agatggccca ccataaagct aaaacttagc ataatcaaac gaataaaaat acctgctgat      480
taaccggttt ttcgcgagag aaccggtttt tttataaaga agcaggaaga taatgtctat      540
tattcatttt taggtgaata acctgcgctg caaattggta tagtttagta ttcaccgggt      600
tattgggcgg gcaaaaaaat ctttgtgaaa tgaaatatt tactttaaaa agactgattg       660
ccggaggtaa tataacagta tgataagtaa tgaaggttca gaaaaagtat tatctccgga      720
agaacaggct aaattacttg gcctgcttaa agggcgtttt gagcaaaata tacaccgcca      780
cgagggcatt gtttgggcta aggtgcaaga aaagcttaag gcagataccc ttaaattgtg      840
gtcattg                                                                847

<210> SEQ ID NO 19
<211> LENGTH: 40
<212> TYPE: DNA
<213> ORGANISM: Dehalospirillum multivorans

<400> SEQUENCE: 19
aggctgtaag aggcgatgaa ggacgtacta gactgcgata                              40
```

```
<210> SEQ ID NO 20
<211> LENGTH: 40
<212> TYPE: DNA
<213> ORGANISM: Dehalospirillum multivorans

<400> SEQUENCE: 20
gctgtaagag gcgatgaagg acgtactaga ctgcgataag                            40

<210> SEQ ID NO 21
<211> LENGTH: 40
<212> TYPE: DNA
<213> ORGANISM: Dehalospirillum multivorans

<400> SEQUENCE: 21
cggttggatc acctcctttc tagagtatag gggcactatc                            40

<210> SEQ ID NO 22
<211> LENGTH: 40
<212> TYPE: DNA
<213> ORGANISM: Dehalospirillum multivorans

<400> SEQUENCE: 22
gcggttggat cacctccttt ctagagtata ggggcactat                            40

<210> SEQ ID NO 23
<211> LENGTH: 40
<212> TYPE: DNA
<213> ORGANISM: Dehalospirillum multivorans

<400> SEQUENCE: 23
tgcggttgga tcacctcctt tctagagtat aggggcacta                            40

<210> SEQ ID NO 24
<211> LENGTH: 40
<212> TYPE: DNA
<213> ORGANISM: Dehalospirillum multivorans

<400> SEQUENCE: 24
ggtcagcggt tcgatcccgc tattctccac cattttttag                            40

<210> SEQ ID NO 25
<211> LENGTH: 40
<212> TYPE: DNA
<213> ORGANISM: Dehalospirillum multivorans

<400> SEQUENCE: 25
gaggtcagcg gttcgatccc gctattctcc accatttttt                            40

<210> SEQ ID NO 26
<211> LENGTH: 40
<212> TYPE: DNA
<213> ORGANISM: Desulfitobacterium frappieri

<400> SEQUENCE: 26
ctggagaagt ctgaagagac ttcgaaatgc cgaagaggca                            40

<210> SEQ ID NO 27
<211> LENGTH: 40
<212> TYPE: DNA
<213> ORGANISM: Desulfitobacterium frappieri

<400> SEQUENCE: 27
agctggagaa gtctgaagag acttcgaaat gccgaagagg                            40
```

```
<210> SEQ ID NO 28
<211> LENGTH: 40
<212> TYPE: DNA
<213> ORGANISM: Desulfitobacterium frappieri

<400> SEQUENCE: 28
agtctgaaga gacttcgaaa tgccgaagag gcaaagcagg                    40

<210> SEQ ID NO 29
<211> LENGTH: 40
<212> TYPE: DNA
<213> ORGANISM: Desulfitobacterium frappieri

<400> SEQUENCE: 29
tgaagagact tcgaaatgcc gaagaggcaa agcaggggaa                    40

<210> SEQ ID NO 30
<211> LENGTH: 40
<212> TYPE: DNA
<213> ORGANISM: Desulfitobacterium frappieri

<400> SEQUENCE: 30
gaagagactt cgaaatgccg aagaggcaaa gcaggggaaa                    40

<210> SEQ ID NO 31
<211> LENGTH: 40
<212> TYPE: DNA
<213> ORGANISM: Actinomycetales Sm-1

<400> SEQUENCE: 31
gcgacgatga tccgcgaaac aagaggacat ggttttcttg                    40

<210> SEQ ID NO 32
<211> LENGTH: 40
<212> TYPE: DNA
<213> ORGANISM: Actinomycetales Sm-1

<400> SEQUENCE: 32
tgatccgcga aacaagagga catggttttc ttgcggtagg                    40

<210> SEQ ID NO 33
<211> LENGTH: 40
<212> TYPE: DNA
<213> ORGANISM: Actinomycetales Sm-1

<400> SEQUENCE: 33
caagaggaca tggttttctt gcggtagggg ttgttgtgtg                    40

<210> SEQ ID NO 34
<211> LENGTH: 40
<212> TYPE: DNA
<213> ORGANISM: Actinomycetales Sm-1

<400> SEQUENCE: 34
tcagcgacga tgatccgcga aacaagagga catggttttc                    40

<210> SEQ ID NO 35
<211> LENGTH: 40
<212> TYPE: DNA
<213> ORGANISM: Actinomycetales Sm-1

<400> SEQUENCE: 35
```
gaggacatgg ttttcttgcg gtaggggttg ttgtgtgttg                                       40

<210> SEQ ID NO 36
<211> LENGTH: 40
<212> TYPE: DNA
<213> ORGANISM: Rhodococcus rhodococcus

<400> SEQUENCE: 36
gttttgtcag cgacgatgat cgggaacgaa ggggttgttt                                       40

<210> SEQ ID NO 37
<211> LENGTH: 40
<212> TYPE: DNA
<213> ORGANISM: Rhodococcus rhodococcus

<400> SEQUENCE: 37
acgatgatcg ggaacgaagg ggttgtttct tcttccggta                                       40

<210> SEQ ID NO 38
<211> LENGTH: 40
<212> TYPE: DNA
<213> ORGANISM: Rhodococcus rhodococcus

<400> SEQUENCE: 38
tttgtcagcg acgatgatcg ggaacgaagg ggttgtttct                                       40

<210> SEQ ID NO 39
<211> LENGTH: 40
<212> TYPE: DNA
<213> ORGANISM: Rhodococcus rhodococcus

<400> SEQUENCE: 39
tcagcgacga tgatcgggaa cgaaggggtt gtttcttctt                                       40

<210> SEQ ID NO 40
<211> LENGTH: 40
<212> TYPE: DNA
<213> ORGANISM: Rhodococcus rhodococcus

<400> SEQUENCE: 40
ggggttgttt cttcttccgg taccggttgt tgtgtgttgt                                       40

<210> SEQ ID NO 41
<211> LENGTH: 40
<212> TYPE: DNA
<213> ORGANISM: Xanthobacter flavus

<400> SEQUENCE: 41
catcgtgaat agggcattga tcgactgtac cgtggcaaca                                       40

<210> SEQ ID NO 42
<211> LENGTH: 40
<212> TYPE: DNA
<213> ORGANISM: Xanthobacter flavus

<400> SEQUENCE: 42
acatcgtgaa tagggcattg atcgactgta ccgtggcaac                                       40

<210> SEQ ID NO 43
<211> LENGTH: 40
<212> TYPE: DNA
<213> ORGANISM: Xanthobacter flavus

<400> SEQUENCE: 43

```
ggtcttgagc gtcttgtccg cgaatatctg tttcgcatgt                           40

<210> SEQ ID NO 44
<211> LENGTH: 40
<212> TYPE: DNA
<213> ORGANISM: Xanthobacter flavus

<400> SEQUENCE: 44
atgacatcgt gaatagggca ttgatcgact gtaccgtggc                           40

<210> SEQ ID NO 45
<211> LENGTH: 40
<212> TYPE: DNA
<213> ORGANISM: Xanthobacter flavus

<400> SEQUENCE: 45
ctcttggggt cttgagcgtc ttgtccgcga atatctgttt                           40

<210> SEQ ID NO 46
<211> LENGTH: 40
<212> TYPE: DNA
<213> ORGANISM: Mycobacterium L1

<400> SEQUENCE: 46
ggtctggggg gtgtgtttgt gtgcttttga tgtgcagttt                           40

<210> SEQ ID NO 47
<211> LENGTH: 40
<212> TYPE: DNA
<213> ORGANISM: Mycobacterium L1

<400> SEQUENCE: 47
gtctgggggg tgtgtttgtg tgcttttgat gtgcagtttc                           40

<210> SEQ ID NO 48
<211> LENGTH: 40
<212> TYPE: DNA
<213> ORGANISM: Mycobacterium L1

<400> SEQUENCE: 48
attgtcaggc gattcgttgg atggcccttt cacctgtagt                           40

<210> SEQ ID NO 49
<211> LENGTH: 40
<212> TYPE: DNA
<213> ORGANISM: Desulfomicrobium norvegicum

<400> SEQUENCE: 49
gcgcccaagc atagcagctt gtgatcattg acagacgaat                           40

<210> SEQ ID NO 50
<211> LENGTH: 40
<212> TYPE: DNA
<213> ORGANISM: Desulfomicrobium norvegicum

<400> SEQUENCE: 50
cagttcgatc ctgttcacct ccaccatttt ccaactcgac                           40

<210> SEQ ID NO 51
<211> LENGTH: 40
<212> TYPE: DNA
<213> ORGANISM: Desulfomicrobium norvegicum
```

<400> SEQUENCE: 51
ctatggcgcc caagcatagc agcttgtgat cattgacaga                                40

<210> SEQ ID NO 52
<211> LENGTH: 40
<212> TYPE: DNA
<213> ORGANISM: Desulfomicrobium norvegicum

<400> SEQUENCE: 52
tatggcgccc aagcatagca gcttgtgatc attgacagac                                40

<210> SEQ ID NO 53
<211> LENGTH: 40
<212> TYPE: DNA
<213> ORGANISM: Desulfomicrobium norvegicum

<400> SEQUENCE: 53
actatggcgc ccaagcatag cagcttgtga tcattgacag                                40

<210> SEQ ID NO 54
<211> LENGTH: 40
<212> TYPE: DNA
<213> ORGANISM: Desulfitobacterium dehalogenans

<400> SEQUENCE: 54
acggagtgga aaaatgccga agaggcaaaa cggagcaatc                                40

<210> SEQ ID NO 55
<211> LENGTH: 40
<212> TYPE: DNA
<213> ORGANISM: Desulfitobacterium dehalogenans

<400> SEQUENCE: 55
cacggagtgg aaaaatgccg aagaggcaaa acggagcaat                                40

<210> SEQ ID NO 56
<211> LENGTH: 40
<212> TYPE: DNA
<213> ORGANISM: Desulfitobacterium dehalogenans

<400> SEQUENCE: 56
tatccacgga gtggaaaaat gccgaagagg caaaacggag                                40

<210> SEQ ID NO 57
<211> LENGTH: 40
<212> TYPE: DNA
<213> ORGANISM: Desulfitobacterium dehalogenans

<400> SEQUENCE: 57
agcatgagca gaagccatag ttgacttatc cacggagtgg                                40

<210> SEQ ID NO 58
<211> LENGTH: 40
<212> TYPE: DNA
<213> ORGANISM: Desulfitobacterium hafniense

<400> SEQUENCE: 58
ctggagaagt ctatagagac ttcgaagtgc cgaagaggca                                40

<210> SEQ ID NO 59
<211> LENGTH: 40
<212> TYPE: DNA
<213> ORGANISM: Desulfitobacterium hafniense

```
<400> SEQUENCE: 59
agctggagaa gtctatagag acttcgaagt gccgaagagg          40

<210> SEQ ID NO 60
<211> LENGTH: 40
<212> TYPE: DNA
<213> ORGANISM: Desulfitobacterium hafniense

<400> SEQUENCE: 60
agtctataga gacttcgaag tgccgaagag gcaaagcagg          40

<210> SEQ ID NO 61
<211> LENGTH: 40
<212> TYPE: DNA
<213> ORGANISM: Desulfitobacterium hafniense

<400> SEQUENCE: 61
tatagagact tcgaagtgcc gaagaggcaa agcaggggaa          40

<210> SEQ ID NO 62
<211> LENGTH: 40
<212> TYPE: DNA
<213> ORGANISM: Desulfitobacterium hafniense

<400> SEQUENCE: 62
atagagactt cgaagtgccg aagaggcaaa gcaggggaaa          40

<210> SEQ ID NO 63
<211> LENGTH: 40
<212> TYPE: DNA
<213> ORGANISM: Clostridium formicoaceticum

<400> SEQUENCE: 63
ggtcaagtta ttaagggcaa agggtggatg ccttggcact          40

<210> SEQ ID NO 64
<211> LENGTH: 40
<212> TYPE: DNA
<213> ORGANISM: Clostridium formicoaceticum

<400> SEQUENCE: 64
gtgcggctgg atcacctcct ttctaaggag aaaggctttt          40

<210> SEQ ID NO 65
<211> LENGTH: 40
<212> TYPE: DNA
<213> ORGANISM: Clostridium formicoaceticum

<400> SEQUENCE: 65
gtgccaaggc atccaccctt tgcccttaat aacttgacct          40

<210> SEQ ID NO 66
<211> LENGTH: 40
<212> TYPE: DNA
<213> ORGANISM: Clostridium formicoaceticum

<400> SEQUENCE: 66
ctcctagtgc caaggcatcc accctttgcc cttaataact          40

<210> SEQ ID NO 67
<211> LENGTH: 40
<212> TYPE: DNA
```

<213> ORGANISM: Clostridium formicoaceticum

<400> SEQUENCE: 67
gcggctggat cacctccttt ctaaggagaa aggcttttac         40

<210> SEQ ID NO 68
<211> LENGTH: 40
<212> TYPE: DNA
<213> ORGANISM: Clostridium formicoaceticum

<400> SEQUENCE: 68
cctagtgcca aggcatccac cctttgccct taataacttg         40

<210> SEQ ID NO 69
<211> LENGTH: 40
<212> TYPE: DNA
<213> ORGANISM: Desulfuromonas chloroethenica

<400> SEQUENCE: 69
ctgtcaggag taaggagaga agagtgagga gtacacctca         40

<210> SEQ ID NO 70
<211> LENGTH: 40
<212> TYPE: DNA
<213> ORGANISM: Desulfuromonas chloroethenica

<400> SEQUENCE: 70
gtgacacgcg aaggtagcaa cacgatcgct taagtagaag         40

<210> SEQ ID NO 71
<211> LENGTH: 40
<212> TYPE: DNA
<213> ORGANISM: Desulfuromonas chloroethenica

<400> SEQUENCE: 71
gagtaaggag agaagagtga ggagtacacc tcaccctaac         40

<210> SEQ ID NO 72
<211> LENGTH: 40
<212> TYPE: DNA
<213> ORGANISM: Desulfuromonas chloroethenica

<400> SEQUENCE: 72
aggagtaagg agagaagagt gaggagtaca cctcacccta         40

<210> SEQ ID NO 73
<211> LENGTH: 40
<212> TYPE: DNA
<213> ORGANISM: Desulfuromonas chloroethenica

<400> SEQUENCE: 73
agtaaggaga gaaagagtgag gagtacacct caccctaacg         40

<210> SEQ ID NO 74
<211> LENGTH: 40
<212> TYPE: DNA
<213> ORGANISM: Desulfuromonas chloroethenica

<400> SEQUENCE: 74
gacacgcgaa ggtagcaaca cgatcgctta agtagaagac         40

<210> SEQ ID NO 75
<211> LENGTH: 40

```
<212> TYPE: DNA
<213> ORGANISM: Acetobacterium woodii

<400> SEQUENCE: 75
ttaacgggac aaataccgga gtagtggtag caggtcccaa                              40

<210> SEQ ID NO 76
<211> LENGTH: 40
<212> TYPE: DNA
<213> ORGANISM: Acetobacterium woodii

<400> SEQUENCE: 76
ccggagtagt ggtagcaggt cccaatcgat cattgaaaac                              40

<210> SEQ ID NO 77
<211> LENGTH: 40
<212> TYPE: DNA
<213> ORGANISM: Acetobacterium woodii

<400> SEQUENCE: 77
gacaaatacc ggagtagtgg tagcaggtcc caatcgatca                              40

<210> SEQ ID NO 78
<211> LENGTH: 40
<212> TYPE: DNA
<213> ORGANISM: Acetobacterium woodii

<400> SEQUENCE: 78
ttttaacggg acaaataccg gagtagtggt agcaggtccc                              40

<210> SEQ ID NO 79
<211> LENGTH: 40
<212> TYPE: DNA
<213> ORGANISM: Acetobacterium woodii

<400> SEQUENCE: 79
tttaacggga caaataccgg agtagtggta gcaggtccca                              40

<210> SEQ ID NO 80
<211> LENGTH: 40
<212> TYPE: DNA
<213> ORGANISM: Dehalobacter restrictus

<400> SEQUENCE: 80
aaggtcaaga tataaagggc atacggtgga tgccttggcg                              40

<210> SEQ ID NO 81
<211> LENGTH: 40
<212> TYPE: DNA
<213> ORGANISM: Dehalobacter restrictus

<400> SEQUENCE: 81
gaaggtcaag atataaaggg catacggtgg atgccttggc                              40

<210> SEQ ID NO 82
<211> LENGTH: 40
<212> TYPE: DNA
<213> ORGANISM: Dehalobacter restrictus

<400> SEQUENCE: 82
aagatataaa gggcatacgg tggatgcctt ggcgccaaga                              40

<210> SEQ ID NO 83
```

```
<211> LENGTH: 40
<212> TYPE: DNA
<213> ORGANISM: Dehalobacter restrictus

<400> SEQUENCE: 83
gcgcgtggca aatttgaact taggagcatc tatgctccgt                           40

<210> SEQ ID NO 84
<211> LENGTH: 40
<212> TYPE: DNA
<213> ORGANISM: Dehalobacter restrictus

<400> SEQUENCE: 84
tcaagatata aagggcatac ggtggatgcc ttggcgccaa                           40

<210> SEQ ID NO 85
<211> LENGTH: 40
<212> TYPE: DNA
<213> ORGANISM: Dehalobacter restrictus

<400> SEQUENCE: 85
tcgcgcgtgg caaatttgaa cttaggagca tctatgctcc                           40

<210> SEQ ID NO 86
<211> LENGTH: 40
<212> TYPE: DNA
<213> ORGANISM: Dehalobacter restrictus

<400> SEQUENCE: 86
cgcgtggcaa atttgaactt aggagcatct atgctccgtc                           40

<210> SEQ ID NO 87
<211> LENGTH: 40
<212> TYPE: DNA
<213> ORGANISM: Desulfitobacterium sp. strain PCE1

<400> SEQUENCE: 87
gtccacctag gcccaccata aaagattgat attgtggggg                           40

<210> SEQ ID NO 88
<211> LENGTH: 40
<212> TYPE: DNA
<213> ORGANISM: Desulfitobacterium sp. strain PCE1

<400> SEQUENCE: 88
agattgatat tgtgggggta tagctcagct gggagagcac                           40

<210> SEQ ID NO 89
<211> LENGTH: 40
<212> TYPE: DNA
<213> ORGANISM: Desulfitobacterium sp. strain PCE1

<400> SEQUENCE: 89
attgatattg tgggggtata gctcagctgg gagagcacct                           40

<210> SEQ ID NO 90
<211> LENGTH: 40
<212> TYPE: DNA
<213> ORGANISM: Desulfitobacterium sp. strain PCE1

<400> SEQUENCE: 90
agagacttct gaaagccgaa gaggcaaaac ggagcaatcc                           40
```

<210> SEQ ID NO 91
<211> LENGTH: 40
<212> TYPE: DNA
<213> ORGANISM: Desulfitobacterium sp. strain PCE1

<400> SEQUENCE: 91
gacttctgaa agccgaagag gcaaaacgga gcaatccgta    40

<210> SEQ ID NO 92
<211> LENGTH: 40
<212> TYPE: DNA
<213> ORGANISM: Desulfitobacterium frappieri TCE1

<400> SEQUENCE: 92
atgcgaattg ataacgtggg ggtgtagctc agttgggaga    40

<210> SEQ ID NO 93
<211> LENGTH: 40
<212> TYPE: DNA
<213> ORGANISM: Desulfitobacterium frappieri TCE1

<400> SEQUENCE: 93
ggataagcac cgatatgctt cggggagtcg caaatagaca    40

<210> SEQ ID NO 94
<211> LENGTH: 40
<212> TYPE: DNA
<213> ORGANISM: Desulfitobacterium frappieri TCE1

<400> SEQUENCE: 94
gatatgcttc ggggagtcgc aaatagacat tgatccggag    40

<210> SEQ ID NO 95
<211> LENGTH: 40
<212> TYPE: DNA
<213> ORGANISM: Desulfitobacterium frappieri TCE1

<400> SEQUENCE: 95
gcaccgatat gcttcgggga gtcgcaaata gacattgatc    40

<210> SEQ ID NO 96
<211> LENGTH: 40
<212> TYPE: DNA
<213> ORGANISM: Desulfitobacterium frappieri TCE1

<400> SEQUENCE: 96
gcactgtgaa atgcgaattg ataacgtggg ggtgtagctc    40

<210> SEQ ID NO 97
<211> LENGTH: 40
<212> TYPE: DNA
<213> ORGANISM: Acetobacterium woodii

<400> SEQUENCE: 97
gtcagttgtt aaggatcaag aaatgaaggg cacagggcgg    40

<210> SEQ ID NO 98
<211> LENGTH: 40
<212> TYPE: DNA
<213> ORGANISM: Acetobacterium woodii

<400> SEQUENCE: 98
gttgttaagg atcaagaaat gaagggcaca gggcggatgc    40

```
<210> SEQ ID NO 99
<211> LENGTH: 40
<212> TYPE: DNA
<213> ORGANISM: Acetobacterium woodii

<400> SEQUENCE: 99
ttgttaagga tcaagaaatg aagggcacag gcggatgcc                         40

<210> SEQ ID NO 100
<211> LENGTH: 40
<212> TYPE: DNA
<213> ORGANISM: Desulfomonile tiedjei DCB-1

<400> SEQUENCE: 100
gattgtcaaa gaactggtgg aggtgaacgg attcgaaccg                        40

<210> SEQ ID NO 101
<211> LENGTH: 40
<212> TYPE: DNA
<213> ORGANISM: Desulfomonile tiedjei DCB-1

<400> SEQUENCE: 101
cgattgtcaa agaactggtg gaggtgaacg gattcgaacc                        40

<210> SEQ ID NO 102
<211> LENGTH: 40
<212> TYPE: DNA
<213> ORGANISM: Desulfomonile tiedjei DCB-1

<400> SEQUENCE: 102
gtcaacctct cagaactgaa tagcagatgt gtgcgttcgg                        40

<210> SEQ ID NO 103
<211> LENGTH: 40
<212> TYPE: DNA
<213> ORGANISM: Desulfomonile tiedjei DCB-1

<400> SEQUENCE: 103
taaccgaact gagctatagg cccgaagccg ttatcgtcaa                        40

<210> SEQ ID NO 104
<211> LENGTH: 40
<212> TYPE: DNA
<213> ORGANISM: Desulfomonile tiedjei DCB-1

<400> SEQUENCE: 104
cgtcaacctc tcagaactga atagcagatg tgtgcgttcg                        40

<210> SEQ ID NO 105
<211> LENGTH: 40
<212> TYPE: DNA
<213> ORGANISM: Desulfomonile tiedjei DCB-1

<400> SEQUENCE: 105
ccgaagccgt tatcgtcaac ctctcagaac tgaatagcag                        40

<210> SEQ ID NO 106
<211> LENGTH: 40
<212> TYPE: DNA
<213> ORGANISM: Dehalococcoides ethenogenes 195

<400> SEQUENCE: 106
tgagcaaaat atacaccgcc acgagggcat tgtttgggct                        40
```

<210> SEQ ID NO 107
<211> LENGTH: 40
<212> TYPE: DNA
<213> ORGANISM: Dehalococcoides ethenogenes 195

<400> SEQUENCE: 107
ttatcaatcg ggccattagc tcagctggtt agagcgcagt                    40

<210> SEQ ID NO 108
<211> LENGTH: 40
<212> TYPE: DNA
<213> ORGANISM: Dehalococcoides ethenogenes 195

<400> SEQUENCE: 108
cgtcacgtca tgaaagccgg taacacttga agtcgatgtg                    40

<210> SEQ ID NO 109
<211> LENGTH: 40
<212> TYPE: DNA
<213> ORGANISM: Dehalococcoides ethenogenes 195

<400> SEQUENCE: 109
gccgcggtaa tacgtaggaa gcaagcgtta tccggattta                    40

<210> SEQ ID NO 110
<211> LENGTH: 40
<212> TYPE: DNA
<213> ORGANISM: Dehalococcoides ethenogenes 195

<400> SEQUENCE: 110
attttgggct gaaggacttg cgctaagcgt cctgtttgct                    40

<210> SEQ ID NO 111
<211> LENGTH: 40
<212> TYPE: DNA
<213> ORGANISM: Dehalococcoides ethenogenes 195

<400> SEQUENCE: 111
ctggatcacc tcctttctaa ggataattgg cctcgtgcct                    40

<210> SEQ ID NO 112
<211> LENGTH: 40
<212> TYPE: DNA
<213> ORGANISM: Dehalococcoides ethenogenes 195

<400> SEQUENCE: 112
gtccttggtt cgagaccaag atggcccacc ataaagctaa                    40

<210> SEQ ID NO 113
<211> LENGTH: 40
<212> TYPE: DNA
<213> ORGANISM: Dehalococcoides ethenogenes 195

<400> SEQUENCE: 113
ggactggtaa ttgggacgaa gtcgtaacaa ggtagccgta                    40

<210> SEQ ID NO 114
<211> LENGTH: 40
<212> TYPE: DNA
<213> ORGANISM: Dehalococcoides ethenogenes 195

<400> SEQUENCE: 114

-continued

```
tgtttggtta agtcctgcaa cgagcgcaac ccttgttgct        40
```

<210> SEQ ID NO 115
<211> LENGTH: 40
<212> TYPE: DNA
<213> ORGANISM: Dehalococcoides ethenogenes 195

<400> SEQUENCE: 115

```
gtcctgataa gactgaggtc cttggttcga gaccaagatg        40
```

<210> SEQ ID NO 116
<211> LENGTH: 20
<212> TYPE: DNA
<213> ORGANISM: Artificial
<220> FEATURE:
<223> OTHER INFORMATION: Sense primer 27F for PCR

<400> SEQUENCE: 116

```
agagtttgat cctggctcag                              20
```

<210> SEQ ID NO 117
<211> LENGTH: 16
<212> TYPE: DNA
<213> ORGANISM: Artificial
<220> FEATURE:
<223> OTHER INFORMATION: Antisense primer 132R for PCR

<400> SEQUENCE: 117

```
gggttbcccc attcrg                                  16
```

<210> SEQ ID NO 118
<211> LENGTH: 20
<212> TYPE: DNA
<213> ORGANISM: Artificial
<220> FEATURE:
<223> OTHER INFORMATION: Antisense primer 341R for PCR

<400> SEQUENCE: 118

```
caatgaccac aatttaaggg                              20
```